United States Patent [19]
Frey et al.

[11] Patent Number: 6,086,881
[45] Date of Patent: Jul. 11, 2000

[54] SPATIALLY ALIGNED CONJUGATED COMPOSITION HAVING A THIOETHER BOND LINKAGE

[75] Inventors: Andreas Frey, Muenster, Germany; Marian R. Neutra, Sherborn, Mass.; Frank A. Robey, Bethesda, Md.

[73] Assignee: Children's Medical Center Corp., Boston, Mass.

[21] Appl. No.: 09/079,374

[22] Filed: May 15, 1998

[51] Int. Cl.[7] .................. A61K 39/385; A61K 38/00; A61M 36/14; C07K 5/00

[52] U.S. Cl. .................. 424/194.1; 530/324; 424/196.11; 424/197.11; 424/1.53; 424/1.69

[58] Field of Search .................. 424/1.69, 1.53, 424/194.1, 196.11, 197.11; 530/323

[56] References Cited

PUBLICATIONS

Fahey t al., Status of immune–based therapies in HIV infection and AIDS, Clin. exp. Immunol. 88, 1–5, see p. 3, col. 2, paragraph 3, Jan. 1992.
Fox, J. L., No winners against AIDS, Bio/Tech. vol. 12, 128, see entire page, Feb. 1994.
Frey et al., Peptomer Aluminum Oxide Nanoparticle Conjugates as Systemic and Mucosal Vaccine Candidates: Synthesis and Characterization of a Conjugate Derived from the C4 Domain of HIV–1 gp120., Bioconjugate Chem. 8, 424–433, see entire article, May 1997.

*Primary Examiner*—Hankyel Park
*Attorney, Agent, or Firm*—David Prashker

[57] ABSTRACT

The present invention is a spatially aligned conjugated composition which comprises at least one chemically modified substance which is immunologically representative of a prechosen infectious agent and provides a chemical constituent for entering into and forming a thioether bond; a plurality of chemically substituted metallic oxide particles which range from about 10–10,000 nanometers and are able to enter into a thioether bond and covalent linkage; and at least one thioether bond and linkage joining the metallic oxide particles in a controlled and spatially aligned manner to the antigen or hapten. The conjugated composition may be alternatively employed as an immunogen; as a vaccine; as a diagnostic tool and reactant; and as an analytical material suitable for testing the pharmacological activity of new compounds.

11 Claims, 8 Drawing Sheets

SPATIALLY ALIGNED CONJUGATED COMPOSITION HAVING A THIOETHER BOND LINKAGE

RESEARCH SUPPORT

This invention was made with government support under Grant Nos. HD17557 and A134757 by the NIH. The government has certain rights in the invention.

FIELD OF THE INVENTION

The present invention is concerned generally with the formation of spatially aligned conjugated compositions in which the component parts are linked in a controlled orientation by at least one thioether bond; and is particularly concerned with the controlled juncture of antigens or haptens to metallic oxide nanoparticles via at least one thioether bond and linkage to form a conjugate useful for a variety of immunological and other biomedical purposes.

BACKGROUND OF THE INVENTION

Among some of the earliest written records of man is an awareness that persons who recover from certain diseases cannot contract them again a second time. In today's terminology, such persons have become immune via a remarkably versatile set of adaptive processes which respond to an immense variety of infectious agents. Immune responses are encountered only in living vertebrates; and such immune responses constitute the principal means of defense against infection by pathogenic microorganisms.

In today's state of knowledge and technology, the infectious agents and the substances presented, produced or released by infectious agents are typically called "antigens". An almost limitless variety of macromolecules can behave as antigens—virtually all proteins; many polysaccharides; nucleoproteins, lipoproteins, and numerous synthetic polypeptides; and many small molecules if they are suitably linked to proteins or to synthetic polypeptides. Classically, an antigen has two properties: immunogenicity—the capacity to stimulate the formation of the corresponding antibodies and/or immune cells; and selectivity—the ability to react specifically with these antibodies or cells. Antigens are also distinct and different from "haptens" which, by definition, are not themselves immunogenic, but do react specifically with the appropriate corresponding antibodies or immune cells.

The term "immunogen" is often used for a substance or composition that stimulates the formation of the corresponding antibody in an organism able to respond. It is clear, however, that immunogenicity itself is not an intrinsic or inherent property of an infectious agent or a macromolecule. To the contrary, immunogenicity is dependent on the system and conditions employed in the introduction of the antigen into the body. One cardinal rule and condition is that the putative immunogen must be somehow recognized as alien, or foreign, or at least not as itself by the responding host.

In addition, for a variety of different public health reasons and medical reasons, man has employed immunogens and many different immunization procedures to increase active in-vivo resistance to infectious agents and to the products of pathogens. This has led to the ever-increasing study and development in the field of a unique problem: how to make and use an effective vaccine. By definition, a vaccine is a preparation used for immunization in which a suspension of infectious agents, some parts of them, or synthetic analogs of them, is given to a living subject in advance of a clinically apparent condition to establish active resistance to an infection or disease. The prevention of clinical infections and pathological disease states via the use of vaccines is considered one of the most effective and available procedures to combat illness. Merely representative of the range and diversity of vaccines available today to prevent infectious disease in man are those listed by Table 1 below.

TABLE 1

Vaccines Preventing Infectious Disease in Man*

| Disease | Immunogen |
| --- | --- |
| Diptheria | purified diptheria toxoid |
| Tetanus | purified tetanus toxoid |
| Smallpox | infectious (attenuated) virus |
| Yellow fever | infectious (attenuated) virus |
| Measles | infectious (attenuated) virus |
| Mumps | infectious (attenuated) virus |
| Rubella | infectious (attenuated) virus |
| Poliomyelitis | infectious (attentuated) virus or inactivated virus |
| Influenza | inactivated virus |
| Rabies | inactivated virus |
| Typhus fever | killed rickettsiae *Rickettsia prowazeki* |
| Typhoid and paratyphoid fevers | killed bacteria *Salmonelta typhi, S. schottmulleri*, and *S. paratyphi* |
| Pertussis | killed bacteria *Bordetella pertussis* |
| Cholera | crude fraction of cholera vibrios |
| Plague | crude fraction of plague bacillus |
| Tuberculosis | infectious (attenuated) mycobacteria (bacille Calmette-Guerin of "BCG") |
| Meningitis | purified polysaccharide from *Neisseria meningitidis* |
| Pneumonia | purified polysaccharides from *Streptococcus pneumoniae* |

*Microbiology, [Davis, Dulbecco, Eisen & Ginsberg, editors], Harper & Row, 1988, p. 448.

Unfortunately, the development of vaccines and vaccination procedures which are effective against microbial antigens and infectious agents is a laborious and almost entirely empiric process. There are very few general rules which are reliable; and even these generalities are meager because they often do not apply uniformly or consistently. Among these are: that the material be antigenic—that is, that the composition contain chemical groupings which are not present in the living recipient and will become accessible to immunologically competent cells of the recipient which is to be immunized. In addition, it is essential that the material employed as a vaccine should have a sufficiently great molecular weight; in general, the larger a molecule is, the greater chance it will have of comprising foreign determinant groups on its surface. Also, it is often desirable that the substances in a vaccine be aggregated or be adsorbed on alum or other gels because these are usually more effective than soluble materials. The aggregated immunogens, by binding more effectively to cells in the living body, and by engaging more cell surface molecules on the specialized cells involved in generating immune responses, are often more stimulatory than dispersed or solute molecules; and the relatively slow rate of desorption from gels or emulsions maintains the antigen in tissues for longer periods of time. There also are variances and conditions regarding systemic versus local immunization procedures—the route of administration and the choice of site for injection being usually determined by convenience, but in some instances being limited by the very nature of the infectious agent, or vaccine efficacy itself, or by the nature or localization of the immune response desired. Finally, the number of administrations or injections of the immunogen used as a vaccine may vary markedly, varying commonly from month-long intervals to responses which last for years or even decades after a single immunization.

Owing to the major differences in the efficacy and usefulness of vaccines generally and to the risks involved in using live attenuated pathogens as vaccines, major research and development efforts have been directed towards the making of synthetic compositions of matter which would provide more effective immunizations and be more readily available for use as vaccines. Merely representative of the more recent innovations in this art are U.S. Pat. Nos. 5,219,577; 5,462,750; 4,251,509; 4,613,500; 5,206,015; 4,744,983; 4,657,762; 4,225,581; 4,329,332; 4,744,760; 4,501,726; 4,904,479; and the different publications cited within each of these issued patents.

In particular also, in any composition which is suitable for use as a vaccine or immunogen, it is essential that the conformational integrity and immunogenic/antigenic sites or "epitopes" of the proteins, macromolecules, or other agents be preserved intact. Changes in the structural configuration, structure, or spatial orientation of these molecules and compounds may and often does result in partial or total loss of antigenic activity and utility. Such changes in configuration are often caused by changing the environment surrounding or containing the compound or agent. Furthermore, the size and the ability of any associated carrier particle to minimize undesireable biological reactions of the recipient subject and to facilitate interaction of the compound with the immune system, are primary concerns when the composition or substance is used under in-vivo conditions. All of these factors must be taken into account when preparing a composition as a conjugate which is to be used as an immunogen and/or as a vaccine or as biomaterial for recognizing specific receptors.

Nevertheless, alterations in spatial orientation or structural alignment, physical denaturation, and other disruptive stereochemical or physical events often do destroy or markedly reduce the efficacy and value of an immunogen and conjugated compositions which have been intentionally prepared for use as a vaccine. Improvements in controlling orientation, overall configuration of the three-dimensional structure and overall size for a substance or prepared conjugate composition are thus of continuing importance and a current major concern in this art. Accordingly, methods and procedures by which such immunogens may be prepared in a chemically controlled manner and in a fixed spatial orientation and alignment are therefore deemed to be most advantageous and beneficial.

SUMMARY OF THE INVENTION

The invention has multiple aspects. A first aspect provides a spatially aligned conjugated composition suitable for use as a vaccine to be administered to a living subject for enhanced immunization against a prechosen infectious agent, said conjugated composition comprising:

at least one chemically modified substance wherein said chemical modification provides said substance with at least one reactive entity and a fixed spatial orientation for forming a thioether bond and wherein said substance is selected from the group consisting of haptens and antigens immunologically representative of the prechosen infectious agent;

a plurality of chemically substituted metallic oxide particles wherein said chemical substitution provides said particles with at least one corresponding reactive moiety capable of forming a thioether bond and wherein said metallic oxide particles have a diameter size ranging from about 10–10,000 nanometers; and at least one thioether bond joining said modified substance in a controlled orientation to said nanometer-sized substituted metallic oxide particles to form a plurality of spatially aligned conjugates.

A second aspect provides a vaccine to be administered to a living subject for enhanced immunization against a prechosen infectious agent, said vaccine comprising:

a biocompatible carrier fluid; and a predetermined quantity of a spatially aligned conjugated composition suspended in said carrier fluid, said spatially aligned conjugated composition being comprised of (i) at least one chemically modified substance wherein said chemical modification provides said substance with at least one reactive entity and a fixed spatial orientation for subsequently forming a thioether bond and wherein said substance is selected from the group consisting of haptens and antigens immunologically representative of the prechosen infectious agent, (ii) a plurality of chemically substituted metallic oxide particles wherein said chemical substitution provides said particles with at least one corresponding reactive moiety capable of forming a thioether bond and wherein said metallic oxide particles have a diameter size ranging from about 10–10,000 nanometers, and (iii) at least one thioether bond joining said modified substance in a controlled orientation to said nanometer-sized substituted metallic oxide particles to form a plurality of spatially aligned conjugates.

BRIEF DESCRIPTION OF THE FIGURES

The present invention can be more easily and completely understood when taken in conjunction with the accompanying drawing, in which.

DETAILED DESCRIPTION OF THE INVENTION

Figure 1:
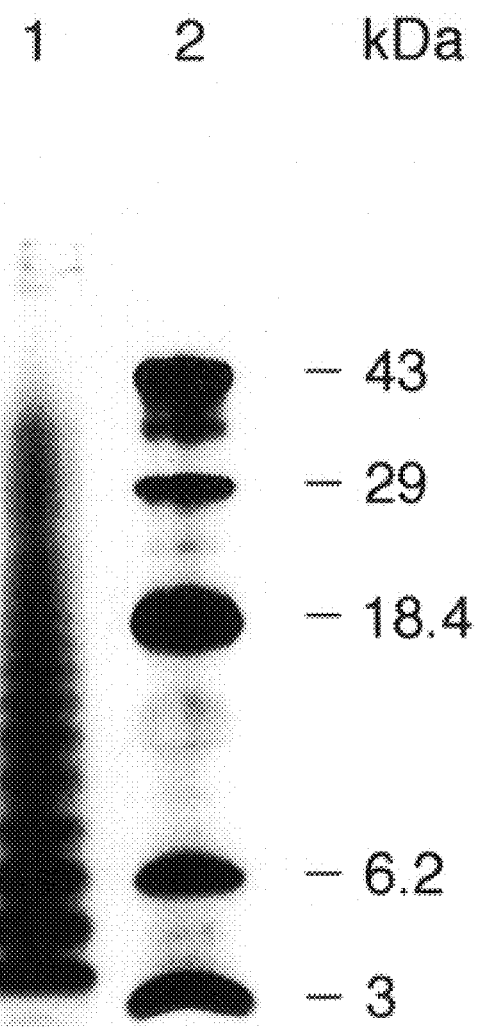
FIG. 1 is a photograph showing an electrophoretic gel analysis of a typical preparation of $HIV_{MN}$ gp120 C4 domain peptomer.

The present invention is an improvement in conjugated compositions which are spatially aligned; demonstrate a fixed orientation and stereochemical configuration with respect to its component parts; and are covalently linked by at least one thioether bond. The conjugated composition provides at least one chemically modified substance which is immunologically representative of a prechosen infectious agent and/or the macromolecular products produced or released by a particular infectious agent. In addition a plurality of chemically substituted metallic oxide particles in nanometer or micrometer diameter size provide a substrate and an aggregate mass upon which the antigen or hapten is disposed. The spatial alignment, chemical structure orientation, and overall chemical configuration for the conjugate molecule as a whole is formed through the presence of at least one thioether bond which joins the modified antigen or hapten in a controlled orientation and covalent linkage to the nanometer-sized metallic oxide particles.

The invention is thus a conjugated or coupled composition of matter, chemically and synthetically produced under controlled chemical conditions to yield a reaction product, whose configuration, conformation, and spatial orientation is controlled, aligned, and permanently fixed. In its broadest aspect and most inclusive delineation, the spatially aligned conjugated composition comprising the present invention has multiple utilities, diverse applications, and provides a variety of highly desirable advantages and benefits.

I. The Value and Utility of the Spatially Aligned Conjugate Composition Comprising the Present Invention The present invention has a primary value and utility as an immunogen and as a vaccine to be administered systemically or locally to a living human or animal subject. The nanometer or micrometer sized metallic oxide particles provide both an anchorage and an underlying substrate particle upon which a chemically modified antigen or hapten immunologically representative of a prechosen infectious agent is deposited and chemically linked via a thioether bond. In this usage and application, the spatially aligned conjugated composition is employed as a vaccine or immunological reagent for raising antibodies in vivo and/or for inducing specific T-cell responses.

In addition, the spatially aligned conjugate composition may be employed as a diagnostic tool in any assay involving antibodies specific for the antigen or hapten indicative of an infectious agent. In this regard, all the conventional in-vitro or ex-vivo assays, methodologies, and techniques may be employed as conventionally reported in the scientific literature wherein the present invention is employed as the specific reagent for antibody binding and detection purposes.

Also, the present invention may be employed for its spatial orientation and structural configuration properties in order to play any role in determining or evaluating the biological activity of novel peptides, proteins, and other pharmacological agents which are ostensibly biologically active. In such usages and applications, it is the spatial alignment, structural integrity, and conformational characteristics provided by the fixed relationship of the antigen or hapten to the anchoring metallic oxide particles which allows such analytical studies to be conducted in order to determine the activity or not of new pharmacological products.

II. The Antigen/Hapten Component of the Conjugated Composition

A requisite component part of the present invention in each and every embodiment is the presence of at least one chemically modified substance having two distinct features; (a) a chemical modification or substitution which provides at least one reactive entity and a fixed spatial orientation for entering into and forming a thioether bond or linkage; and (b) a substance which is either a hapten or antigen and which is immunologically representative of a prechosen infectious agent, or the products produced by or released from an infectious agent. Both of these features and requirements are critical and essential.

It will be noted that the substance is thus an infectious microbe or microorganism which is present in whole or in part, and provides antigenic determinants or epitopes which are immunologically representative or illustrative of a particular infectious agent. Merely representative of the range and variety of infectious agents encompassed by this definition and expected to be employed as a component part in the spatially aligned conjugated composition of the present invention are those bacterial, mycotic, parasitic and viral agents listed by Table 2 below.

TABLE 2

Infectious Agents of Man and Animals

Viral Infectious Agents:

DNA-Viruses:

Adeno viruses
Hepadna viruses
Herpes viruses
Papova viruses
Parvo viruses
Pox viruses
RNA-Viruses:

Arena viruses
Bunya viruses
Corona viruses
Orthomyxo viruses
Paramyxo viruses
Picorna viruses
Reo viruses
Retro viruses
Rhabdo viruses
Toga viruses
Unclassified Viruses:

As yet unclassified oncogenic viruses
Gastroenteritis viruses
Hepatitis viruses
  Bacterial Infectious Agents:

Cocci:

Branhamellae
Neisseriae
Staphylococci
Streptococci
Bacilli:

Baeteroides
Clostridia
Bacilli
Bordetellae
Brucellae
Campylobacters
Corynebacteria
Escherichiae
Francisellae
Haemophili

TABLE 2-continued

Infectious Agents of Man and Animals

Helicobacters
Legionellae
Listeriae
Fusobacteria
Pasteurellae
Pseudomonads
Salmonellae
Shigellae
Vibrios
Yersiniae
Spirochetes:

Borreliae
Leptospirae
Treponemae
Actinomycetes:

Actinomycetae
Mycobacteriae
Nocardiae
   Rickettsiae:

Coxiellae
Rickettsiae
   Chlamydiae

Mycoplasms

Fungal Infectious Agents:

Aspergilli
Candidae
Coccidiae
Cryptococci
Histoplasmae
   Parasitic Infectious Agents:

Babesiae
Cryptosporidii
Eimeriae
Entamoebae
Giardia
Plasmodii
Toxoplasmidae
Trypanosomae Accordingly, the chemical nature and composition of the substance employed as the antigen or hapten in the conjugate composition may be proteinaceous—that is a peptide, polypeptide or protein fragment of any size, origin, or molecular weight which provides at least one antigenic determinant or epitope. Alternatively, the substance may in fact be a polysaccharide in composition as is the case with certain surface antigens of *streptococcus pneumoniae* or *Neisseria meningitidis*. Equally important, the modified substance may be naturally obtained or chemically synthesized; be a fragment or the entirety of a particular protein or polysaccharide component of the infectious agent; and may include the entirety of the infectious microbe itself in the extreme cases.

In addition, it is required that the substance which is immunologically representative of the specific infectious agent be chemically modified to provide a substituent able to react in forming at least one thioether bond and covalent linkage on-demand. It is preferable to chemically modify certain functional groups of the substance which in most instances is expected to be of proteinaceous or polysaccharide nature into thiol-reactive or thiol-containing moieties in a way such that the remainder of the substance is unaffected and unchanged as a consequence of the chemical modification and substitution. Such a thiol-reactive functionalization may be achieved by but is not confined to the means of haloacetylation or derivatization with $\alpha,\beta$-unsaturated compounds, epoxy compounds or aziridine compounds. Thiol-containing groups may be introduced by but are not confined to the reaction with iminothiolane, cysteamine, cysteine, N-acetylhomocysteinethio-lactone, 4-(4-N-maleimidophenyl)butyric acid hydrazide or 2-acetamido-4-mercaptobutyric acid hydrazide. In the alternative, endogeneous cysteine amino acids and the disulfide linkages contained therein may also be employed for creating the thioether bond and linkage on-demand.

III. The Nanometer-Sized Metallic Oxide Particles

The second requisite component part of each embodiment comprising the present invention is the presence of a plurality of metallic oxide particles. There are two requisite features and characteristics for this component part of each conjugated composition: (a) that the particles be of a diameter size ranging from about 10–10,000 nanometers and preferably 100–500 nanometers; and (b) that the metallic oxide particles be chemically substituted and altered such that the chemical substitution provides the particles with at least one, and preferably a multiplicity of, corresponding reactive moieties capable of entering into and forming a thioether bond and linkage on-demand. Each of these features and characteristics will be described in detail.

The metallic oxide particles suitable for use comprise at least one selected from the group consisting of aluminum oxide ($Al_2O_3$), titanium dioxide ($TiO_2$), zirconium dioxide ($ZrO_2$), hydroxyapatite ($Ca_{5(OH)}(PO_4)_3$), silicon dioxide ($SiO_2$), magnesium oxide (MgO), yttrium oxide ($Y_2O_3$), scandium oxide ($Sc_2O_3$), lanthanum oxide ($La_2O_3$) and mixed oxides of the above, as the preferred embodiments. Other metallic oxides may also be utilized provided that these are biocompatible and provide inorganic particles suitable for use as a anchorage or substrate for depositing an antigen or hapten in a spatially aligned manner. Of these, aluminum oxide particles are the most desirable choice for in-vivo usages and applications, especially when the conjugated composition is to be employed either as an immunogen or a vaccine.

The size requirements for the metallic oxide particles are important when forming a spatially aligned conjugated composition in accordance with the present invention. The permissible range of diameter size of between 10–10,000 nanometers provides a useful range of average diameter sizes which are both effective and desirable. In general, the 300 nanometer diameter size is most preferred; and a variance of about 40–900 nanometer size generally provides sufficient consistency and uniformity of diameter size for most practical use circumstances and applications.

The requirement that the metallic oxide nanoparticle be chemically substituted with at least one reactive moiety capable of forming a thioether bond on-demand is easily satisfied using conventionally known chemical techniques and reactions. Owing to the nature of the metallic oxide as an inorganic chemical composition harsh chemical reaction conditions may be employed to introduce the desired thiol or thiol-reactive groups. For that reason it is preferred to prepare the thiol-containing or thiol-reactive metallic oxide nanoparticles in the absence of the biomolecule component. The proteinaceous or polysaccharide constituent may then be coupled in a single step onto the metallic oxide particles via the formation of at least one thioether bond or it may be synthesized or assembled stepwise onto the metallic oxide particles after the initial thioether bond formation.

Accordingly, the chemical derivatization reagents for the metallic oxide particles typically include organosilane reagents that provide thioalkane functionality or other groups that may readily be converted into thiols or thiol-reactive moieties. Organosilane reagents which may be utilized for this purpose may be, but are not limited to, 3-mercaptopropyltrimethoxysilane, 3-aminopropyltriethoxysilane, 3-iodopropyltrimethoxysilane, 2-chloroethyltrichlorosilane, 3-glycidoxypropyltrimethoxysilane, vinyltrichlorosilane, 3-acryloxypropyltrimethoxysilane. In addition, any number of moieties containing one or more disulfide components may also be joined to the metallic oxide particle surface and thereby provide the corresponding reactive moiety able to enter into and form a thioether bond and juncture.

IV. The Thioether Bond and Linkage Requirement for the Conjugated Composition By definition, a thioether is a sulfide (RSR) and is the thiol-analog of an oxygen-containing ether. The systematic naming utilizes thio in place of oxy-; and thus the term "thioether" is commonly used as often as the term "sulfide".

The formation of thioethers (or sulfides) is conventionally known chemistry and is commonly described in many textbooks of organic chemistry in particular. Among the conventional reactants and reaction schemes traditionally employed in the generation of thioether bonds and thioether containing products are those provided by Table 3 below.

TABLE 3

Conventional Reactions For Preparing Thioether Bonds

Addition of thiols to α,β-unsaturated compounds

Ia 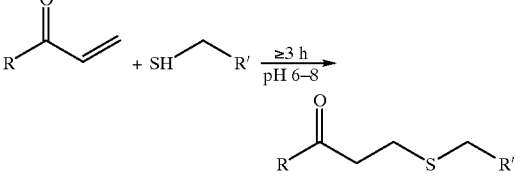

Ib 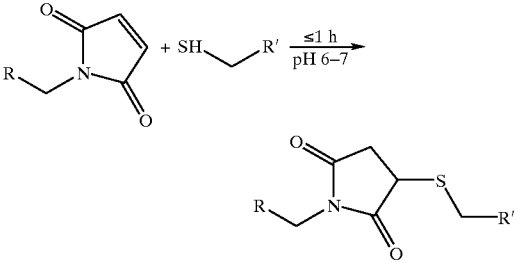

Ic 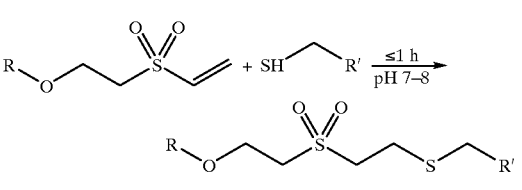

TABLE 3-continued

Conventional Reactions For Preparing Thioether Bonds

Nucleophillic substitution of haloacetyl compounds by thiols

II 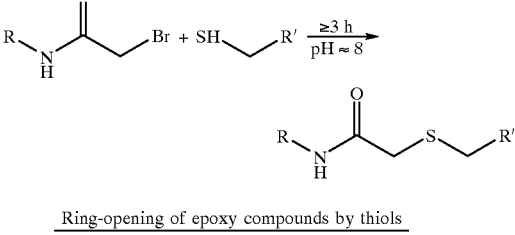

Ring-opening of epoxy compounds by thiols

III 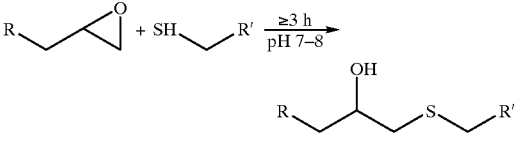

Ring-opening of aziridine compounds by thiols

IVa 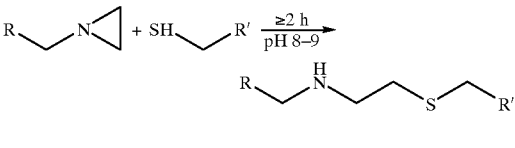

IVb 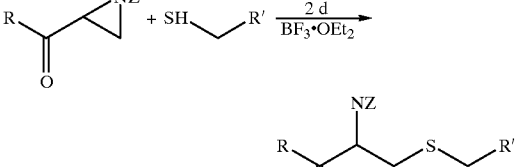

IVc 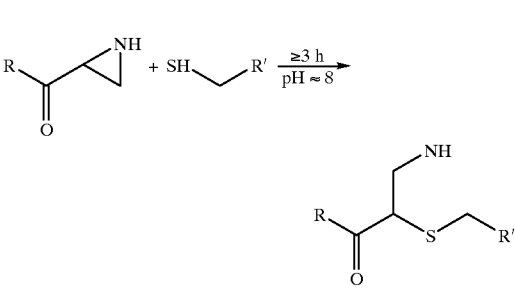

References to thioether formation procedures:
Ia: see textbooks on organic chemistry; Prendergast et al., J. Biol. Chem. 258: 7541–7544 (1983).
Ib: Gregory, J. Am. Chem. Soc. 77: 3922–3923 (1955); Gorin et al., Arch. Biochem. Biophys. 115: 593–597 (1966); Hashida et al., J. Appl. Biochem. 6: 56–63 (1984); Bhatia et al., Anal. Biochem. 178: 408–413 (1989).
Ic: Houen and Jensen, J. Immunol. Methods 181: 187–200 (1995); Morpurgo et al., Bioconjugate Chem. 7: 363–368 (1996).
II: see experimental section and citations therein; Bhatia et al., Anal. Biochem. 178: 408–413 (1989).
III: see textbooks on organic chemistry; Hsu and Huang, J. Non-Cryst. Solids 208: 259–266 (1996).
IVa: Nakajima et al., Bull. Chem. Soc. Jpn. 56: 520–522 (1983); Parry et al., J. Am. Chem. Soc. 107: 2512–2521 (1985); Kogami and Okawa, Bull. Chem. Soc. Jpn. 60: 2963–2965 (1987).
IVb: Scouten et al., Biochim. Biophys. Acta 336: 421–426 (1974); Lankmayr et al., Fresenius Z. Anal. Chem. 295: 371–374 (1979).
IVc: Hata and Watanabe, Tetrahedron 43: 3881–3888 (1987); Moroder et al., FEBS Lett. 299: 51–53 (1992).

In addition, the present invention envisioned that many other different types of reactions and reaction schemes capable of creating and forming a thioether bond and linkage on-demand are possible and may be usefully employed. Thus, regardless of the particular substituents or chemical reactants actually used, so long as at least one thioether bond and linkage is formed and demonstrably exists such that the antigen/hapten representative of the infectious agent is joined via at least one thioether bond to the metallic oxide nanoparticles, any chemical moiety, substituent, or modification is expressly within the scope of the present invention.

V. The Formulation of a Vaccine Using the Present Invention

It is desirable and often necessary that the spatially aligned conjugated composition prepared as described herein must or should be dispersed or suspended in a fluid carrier in order to utilize the conjugated composition as a vaccine. The fluid carrier allows hydration of the antigenic molecules to be maintained, an important consideration for maintaining the native folding or conformation of the antigenic substance. Thus, it is expected and intended that the carrier fluid be one which is biocompatible with the physiology and body of the living subject; and also be a fluid which should be effectively inert or quiescent physiologically and pharmacologically such that the fluid serves as a carrier alone.

The choice of carrier fluid typically varies with the route of administration intended to be used and the nature of the surface cells or tissues at the site at which the spatially aligned conjugated composition actually enters the body of the living subject. Accordingly, a systemic administration includes parenteral routings which typically include intravenous, intramuscular, and intraperitoneal administrations on single or multiple occasions. Typically such administration utilizes a syringe or other direct instrument access; and the traditional carrier fluids include physiological strength saline, 5% dextrose solutions; serum; and other blood compatible fluids whether naturally occurring or artificially synthesized.

In addition, the present invention also expects and is intended for localized routes of administration—such as mucosal administrations via the intragastrical, nasal, rectal, oral, and/or vaginal routes. The traditional formulations and carriers suitable for administration to mucous membrane tissues thus typically include oil-based formulations using petrolateum, mineral oil and/or water-in-oil emulsions as well as aqueous based gels, lotions, and other liquids. The particular strength, concentration, and formulations are classically found and described in both the U.S. and British Pharmacopeias (the texts of which are expressly incorporated herein).

Accordingly, while aqueous based fluid carriers are usual and preferable, a number of oil based semi-solids, gels, and other formulations may be alternatively employed as a carrier fluid for immunization and vaccine purposes.

VI. Experiments and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative and representative of the scope of the invention envisioned and claimed.

It will be recognized that the experiments and data presented hereinafter are directed to human immunodeficiency virus type 1 (HIV-1); and that the prepared spatially aligned conjugated composition is intended for use as a vaccine which is to be administered via injection or delivery to the mucosal surfaces in the body of a living subject. Other intended uses and applications of the present invention as a whole are not nearly so stringent and demanding.

EXPERIMENTAL BACKGROUND

Human immunodeficiency virus type 1 (HIV-1) is a pathogen that is transmitted by direct entry via needles or damaged tissue, or across the mucosal surfaces of the urogenital tract and the rectum [DeSchryver and Meheus, *Bull. W.H.O.* 68: 639–654 (1990)]. To intercept the virus on all routes of infection, vaccines must be developed that induce both mucosal and systemic immune responses against HIV-1 [Forrest, *Vaccine Res.* 1: 137–142 (1992); Marx et al., *Science* 260: 1323–1327 (1993)]. Systemic immune responses include serum antibodies and cytotoxic T cells in blood and tissues. An important component of mucosal immune protection is antigen-specific secretory immunoglobin A (sIgA); these are dimeric or polymeric molecules that are secreted onto mucosal surfaces where they bind pathogens, trap them in mucus, and prevent their further progression. An HIV-1 vaccine should also be able to induce strong systemic humoral and cell-mediated immunity to arm the body against the virus if it breaches the mucosal barrier.

A sIgA response is most effectively induced only when an antigen is delivered to the immune system via mucosal surfaces. In the intestine and rectum, antigens, non-living particles and living pathogens are taken up by M cells, a specialized epithelial cell type that occurs exclusively in the epithelium over organized mucosa-associated lymphoid tissue. Selective uptake by M cells is demonstrably enhanced when the antigen is formulated as a micro- or nanoparticulate material ideally of 0.05–1 $\mu$m diameter, since only M cells are able to translocate particles of such a size across the tight epithelial barrier [Neutra et al., *Cell* 86: 345–348 (1996) and *Annu. Rev. Immunol.* 14: 275–300 (1996); Frey et al., *J. Exp. Med.* 184: 1045–1059 (1996)]. Soluble antigens in the size range of oligopeptides and small proteins are less desirable since they may be taken up by epithelial lining cells and give rise to a state of immunological unresponsiveness that is called oral tolerance [Bland and Warren, *Immunology* 58: 9–14 (1986)]. Formulating the antigen in particulate form also is beneficial for systemic vaccinations since mononuclear phagocytes, like macrophages and Kupffer cells, efficiently phagocytose, process and present antigens that appear in such a particulate form.

When antibody-mediated protection against intact pathogens is desired, as for the protection of the mucosal surfaces by sIgA, it is essential that the vaccine be formulated to closely resemble the native structure and conformation of the antigen targets. The native structure and conformation of protein antigens can be altered by aggregation and improper folding as well as by denaturation and breakdown during the formulation procedure. In addition, antigenic variation in the wild-type pathogen may reduce efficacy of any vaccine based on protein antigens generated in the laboratory.

The development of an effective vaccine against HIV-1 hinges on all of these factors. For effective protection against HIV-1, the antibody response must be directed against the viral envelope glycoproteins gp120 or gp41. Antibodies directed against certain epitopes within the HIV-1 gp120 and gp41, however, were shown to enhance infection of macrophages and monocytes in culture [Takeda et al., *Science* 242: 580–583 (1988)] and to crossreact with immune-relevant host proteins such as HLA-DR [Lasky et al., *Cell* 50: 975–985 (1987); Golding et al., *J. Exp. Med.* 167: 914–923 (1988)] as well as certain immunoglobin subclasses [Bjork, *Immunol. Lett.* 28: 91–96 (1991)]. Furthermore, both of these envelope proteins evade the immune surveillance of the body by continuous variation of their antigenic sites.

On the virus surface, the envelope proteins gp120/41 are assembled in complex oligomeric structures [Earl et al., *Proc. Nat. Acad. Sci. USA* 87: 648–652 (1990)] in which the second and third variable regions (V2 and V3) and a segment of the fourth constant region (C4) of gp120 are exposed [Moore et al., *J. Virol.* 68: 469–484 (1994)]. Among those, the C4 region is of particular importance for the virulence of the virus because it is part of the binding site that interacts with the viral receptor CD4 [Lasky et al., *Cell* 50: 975–985 (1987); Cordonnier et al., *Nature* 340: 571–574 (1989)]. As numerous monoclonal antibodies against the C4 region are neutralizing and broadly cross-reactive between different HIV-1 isolates, this C4 region is an attractive candidate for an HIV-1 subunit vaccine.

However, synthetic C4 peptides do not bind CD4 without being in a solution containing helix-inducing substances such as certain nonionic detergents [Robey et al., *J. Biol. Chem.* 271: 17990–17995 (1996)]; and antibodies raised against monomeric C4 peptides do not recognize native or recombinant gp120 glycoprotein [Robey et al., *J. Biol. Chem.* 270: 23918–23921 (1995)]. The reason for this is that monomeric C4 peptides display a random coil or β-sheet structure. Polymerizing the monomer head-to-tail in a coordinate manner renders the product predominantly α-helical. In the presence of the proper adjuvant, this α-helical polymer is capable of inducing antibodies that recognize recombinant as well as native gp120 [Robey et al., op. cit., 1995). In contrast, polymerizing the monomer randomly (head-to-tail/tail-to-head) and immunizing using Freund's adjuvant (which could denature secondary structures) did not produce antibodies that recognized intact gp120 [Sastry and Arlinghaus, *AIDS* 5: 699–707 (1991)]. Thus, if C4 is used in a vaccine formulation it should not only be polymeric but also be delivered in a nondenaturing environment in order to maintain its α-helical conformation.

Aluminum oxohydroxide, phosphate and hydroxyphosphate compounds are hydrophilic, particulate adjuvants with a long history of safety and efficacy for systemic vaccination [Hem and White, *Pharm. Biotechnol.* 6: 249–276 (1995); Gupta et al., *Pharm. Biotechnol.* 6: 229–248 (1995)]. However, the drawbacks of these substances for oral administration are their pH lability, the noncovalent adsorption of the antigen to their surfaces; and the rapid release of the antigen from the adjuvant after injection. When administered orally, antigen dispensed in these adjuvants may readily dissociate during gastrointestinal passage—thereby rendering the vaccine preparation ineffective.

To circumvent the problems associated with the gel-type aluminum compounds, a composition of matter was prepared in which the antigen of choice is an HIV-$1_{MN}$ gp 120 C4 domain peptomer that is covalently conjugated onto the surface of calcinated aluminum oxide nanoparticles. In the experimental series I, presented hereinafter, the synthesis and characterization of this spatially aligned conjugate composition is described with special emphasis on its immunologically relevant properties—such as particle diameter, antigen load and degree of polymerization of the individual C4 domain oligopeptide units. In the experimental series II, the immunological properties of this synthesized, spatially-aligned conjugate composition were evaluated in a systemic and mucosal immunization study.

Experimental Series I

A. Materials

Reagents for particle, peptide and peptomer synthesis:

α-aluminum oxide nanoparticles were purchased from Fluka (Ronkonkoma, N.Y.). (3-Aminopropyl)-triethoxysilane (98%) and nitric acid, anhydrous toluene, toluene and acetone (all ACS grade) were from Aldrich Chemical (Milwaukee, Wis.). Deionized ultrapure water was prepared using a Millipore water purification system (Millipore, Bedford, Mass.). All chemicals used for peptide synthesis were from Applied Biosystems (Foster City, Calif.). Bromoacetic acid (99+%), N-acetylhomocysteinethiolactone (99%) were obtained from Aldrich Chemical. N-succinimidyl bromoacetate was synthesized as described previously by Bernatowicz and Matsueda [*Anal. Biochem.* 155: 107–112 (1986)].

Materials and reagents for amino acid analysis, SDS-PAGE analysis and electron microscopy:

Chemicals for the preparation of aqueous buffers and solutions were obtained from various sources in the highest quality commercially available (Sigma Chemical, St. Louis, Mo.; Fisher Scientific, Pittsburgh, Pa.; Aldrich Chemical; Calbiochem-Novabiochem, San Diego, Calif.). Tris-tricine 10–20% polyacrylamide gels were from Novex (San Diego, Calif.), and prestained low range protein molecular weight standards from Gibco-BRL (Gaithersburg, Md.). Polyvinylformal (Formvar 15/95) and 150 square mesh copper grids were purchased from Polysciences, Inc. (Warrington, Pa.).

B. Synthesis Procedures

Synthesis of the $HIV_{MN}$ gp120 C4 domain pertomer:

The general methods for preparing peptomers and their monomrneric peptide building blocks have been described in detail previously [See for example Robey and Fields, *Anal. Biochem.* 177: 373–377 (1989); and Robey, F. A., In: *Methods in Molecular Biology*, Vol. 35, 1994, pp. 73–91]. In brief, cysteine-containing peptide monomers were synthesized on p-methyl-PAM resin using the standard BOC technology on an Applied Biosystems model 430A automated peptide synthesizer on a 0.5 mMol scale. In the last step of the synthesis of the peptide chain, bromoacetic acid anhydride was reacted with the amino terminal acid to form the N-α-bromoacetyl-derivatized, fully protected peptide. Deprotection and release of the bromoactylated peptide from the resin were accomplished by treating the resin with anhydrous hydrogen fluoride containing 10% (v/v) m-cresol. After evaporation of the hydrogen fluoride the residual resin-peptide mixture was extracted with ethyl acetate followed by extraction of the peptide in 0.1 M acetic acid. The peptide solution was separated from the resin by filtration and dried by lyophilization. Purification of the peptide was accomplished by preparative reversed phase HPLC on a Vydac C18 column using a 0.1% aqueous trifluoroacetic acid/acetonitrile gradient. The purified peptide was lyophilized and stored at room temperature in the dark. The N-α-bromoacetyl-derivatized $HIV_{MN}$ gp120 C4 domain peptide was obtained in yields between 50 and 70%.

To form the $HIV_{MN}$ gp120 C4 domain peptomer, typically 10 mg purified N-α-bromoacetyl-derivatized peptide was dissolved in 1 mL of deoxygenated 10 mM Ths-HCl, 1 mM EDTA, pH 8.0, and allowed to autopolymerize for 21 h at room temperature under continuous stirring. The reaction was terminated by dialysis against water followed by dialysis against 0.1 M sodium bicarbonate, both at 40° C. using 15,000 MWCO dialysis tubing (Spectrum, Houston, Tex.). The peptomer was then end-capped by first reacting it with 10 μL/mL (143 mM) β-mercaptoethanol followed by 32 mg/mL (173 mM) iodoacetamide, each for 1 h at room temperature under continuous stirring. The end-capped peptomer was dialyzed against 0.1 M sodium acetate followed by deionized water, both at 4° C. At that stage, the peptomer solution was either used directly for bromoacetylation of lysines with N-succinimidyl bromoacetate or it was lyophilized for long term storage. When lyophilized, the sodium acetate form of the peptomer was a dry white powder which was stored desiccated at room temperature. Typical yields were 80 to 90% (referring to the initial amount of N-α-bromoacetyl-derivatized peptide).

Bromoacetylation of the $HIV_{MN}$ gp120 C4 domain peptomer:

12.4 mg (52.5 $\mu$Mol) N-succinimidyl bromoacetate were dissolved in 124 $\mu$L DMF, and 22.4 $\mu$L (~9 $\mu$Mol ester) of this solution were added to a solution of 20 mg $HIV_{MN}$ gp120 C4 domain peptomer (~26 $\mu$Mol free side chain amine) in 20 mL water. After 15 min incubation at room temperature the reaction was terminated by extensively dialyzing against $O_2$-free deionized water at room temperature. The resulting 20 mL of 1 mg/mL bromoacetylated peptomer in water were used directly to react with the thiol-derivatized particles: derivatization yield, 28% of the free side chain amine (~80% of the theoretical value referring to the amount of N-succinimidyl bromoacetate).

Surface activation of the aluminum oxide nanoparticles:

The cleaning and surface activation of the alumina was carried out as recommended by Weetall, H. H. [*Methods Enzymol.* 44: 134–148 (1976)]. In a 2 L Erlenmeyer-flask, 126.7 g (1.24 Mol) α-aluminum oxide nanoparticles (300 nm nominal diameter, calcinated at 1300° C., 99.99% pure, >95% α-form) were suspended in 1140 mL 5% (w/v) nitric acid and heated under swirling for 90 min at 88° C. The slurry then was allowed to cool to 0° C. in an ice-water bath for 90 min before it was transferred into polyallomer centrifuge bottles, centrifuged at 1500×g for 10 min at 4° C. and the supernatant was aspirated. To wash the particles, they were resuspended mechanically in deionized ultrapure water at room temperature, centrifuged at 9500×g for 15 min at 4° C. and the supernatant was removed by aspiration. After a total of 10 washes in 440 mL deionized ultrapure water each, the particle sediment was transferred into a nitric acid-cleaned glass beaker, dried at 250° C. until the weight was constant (21 h), pulverized in a nitric acid-cleaned mortar and stored desiccated at room temperature in a nitric-acid cleaned glass bottle: yield, 112.2 g (88.6%).

Amine-modification of the activated aluminum oxide nanoparticles:

The amine-modification of the alumina was adopted from the procedures described by Weetall (1976) cited above. In a 2 L round bottom flask, 50.2 g (0.49 Mol) of surface activated, dry aluminum oxide nanoparticles were suspended in 450 mL anhydrous toluene, 50 mL (0.21 Mol) (3-aminopropyl)-triethoxysilane were added and the mixture was refluxed under anhydrous conditions for 23 h at 135° C. in an oil bath. Then the suspension was allowed to cool to ambient temperature over 3 h before it was transferred into polyallomer centrifuge bottles, centrifuged at 200×g for 5 min and the supernatant was aspirated. To wash the particles, they were resuspended mechanically in 450 mL fresh toluene at room temperature, centrifuged and the supernatant was removed by aspiration. After 5 washes in toluene, 450 mL each, (centrifugation conditions: 200×g, 5 min, 4° C.) followed by 3 washes in acetone, 450 mL each, (centrifugation conditions: 5000×g, 20 min, 4° C.) the particle sediment was transferred to a nitric acid-cleaned glass beaker and dried for 17 h under vacuum at room temperature followed by 22 h at 115° C. and normal pressure. Then the sediment was pulverized in a nitric acid-cleaned mortar and the amine-modified nanoparticles were stored desiccated at room temperature in an amber bottle: yield, 48.1 g (96% referring to the weight of the underivatized surface activated particles); amine load, 15.9 $\mu$Mol $R\text{-}NH_2$/g solid.

Thiol derivatization of the amine-modified aluminum oxide nanoparticles:

250 mg (1.57 mMol) N-acetylhomocysteinethiolactone were added to 1 g of amine-modified aluminum oxide nanoparticles (15.9 $\mu$Mol $R\text{-}NH_2$) in 10 mL $O_2$-free 0.1 M sodium borate buffer, pH 10, in a 13-mL polypropylene tube. The tube was placed on a rotator and the reaction was allowed to proceed at room temperature for 45 min under constant rotation at 30 rpm. The particles were then washed by centrifuging the buffer-particle mixture at 300×g for 5 min at room temperature and resuspending the sediment in $O_2$-free phosphate-buffered saline (PBS). This washing procedure was repeated twice and the particles were finally suspended in 1 mL $O_2$-free PBS.

Coupling of bromoacetylated $HIV_{MN}$ gp120 C4 domain peptomer to thiol-derivatized aluminum oxide nanoparticles:

20 mL of a solution of 1 mg/mL bromoacetylated peptomer (~7.3 $\mu$Mol bromoacetyl residues) in water were added to 1 mL thiol-derivatized particles suspended in PBS (700–800 mg solids) in a 50-mL conical polypropylene tube. The mixture was placed on a rotator and mixed at room temperature for 1 hr under constant rotation at 30 rpm. Then, 1 mL $O_2$-free 0.1 M sodium bicarbonate was added and the reaction was allowed to proceed for another 65 h. The suspension was the centrifuged at 3000×g for 20 min at room temperature and the resulting sediment was washed 3× in PBS and 5× in deionized water by resuspending and then centrifuging at 4° C. The final sediment was lyophilized and stored desiccated at room temperature: yield, 684 mg peptomer nanoparticles containing 16 mg peptomer/g particles (55% of the theoretical value).

C. Analytical Procedures

Analysis of the aluminum oxide nanoparticle derivatives:

The amount of free amine that was covalently linked to the aluminum oxide particles was determined with the ninhydrin method of Sarin et al., [*Anal. Biochem.* 117: 147–157 (1981)]. The presence of free sulfhydryl groups on the modified aluminum oxide that were formed after the reaction of the free amine with N-acetylhomocysteinethiolactone was determined using Ellman's reagent; and the amount of peptide conjugated to the aluminum oxide particles was determined by amino acid analysis using the Waters Picotag® HPLC system (Waters Corp., Milford, Mass.).

SDS-polyacrylamide gel analysis of peptomer preparations:

Peptomer in sample buffer [2% (w/v) sodium dodecylsulfate, 10% (v/v) glycerol, 20% (v/v) β-mercaptoethanol, 0.01% (w/v) bromphenoiblue] was denatured for 4 min at 100° C., loaded (1–1.5 $\mu$g/lane) onto tris-tricine 10–20% polyacrylamide gradient/SDS gels and run for 2 h at 40–50 mA in tris-tricine electrophoresis buffer (12.1 g/L tris base, 17.9 g/L tricine, 1 g/L sodium dodecylsulfate). Gels were fixed for 3.5 hr in 10% (v/v)

acetic acid, 30% (v/v) methanol, and silver-stained according to the method of Oakley et al., [*Anal. Biochem.* 105: 361–363 (1980)].

Circular Dichroism of Peptomer Preparations:

CD spectra of the peptides, peptomers and N-ε-bromoacetylated peptomers were studied using a Jasco Model J-500A/DP-501N CD spectropolarimeter with peptides and peptomers in 10 mM phosphate buffer pH 7.2 as described previously by Robey et al., [*J. Biol. Chem.* 270: 23918–23921 (1995)].

Densitometry:

To determine the relative amounts of individual peptide oligomers in the peptomer preparations a photographic reproduction of a silver-stained peptomer polyacrylamide gradient gel was scanned with a Microtek Scanmaker III scanner (Microtek Lab Inc., Redondo Beach, Calif.) at 600×600 dpi and analyzed with the NIH Image software package (National Institutes of Health, Bethesda, Md.) after one-dimensional vertical background subtraction on an Apple Power PC 7100/66 computer (Apple Inc., Cupertino, Calif.).

Electron microscopy and particle size determination:

5 mg of surface-activated aluminum oxide nanoparticles, amine-modified nanoparticles or peptomer-conjugated nanoparticles were suspended in 1 mL deionized water by agitation and brief sonication (1–2×5 sec) in a water bath sonicator (Sonorex RK510S, Bandelin electronic, Berlin, FRG). The suspensions were serially diluted to concentrations of 500, 50 and 5 μg/mL particles in water, with sonication between each dilution step.

For transmission electron microscopy (TEM), 10 μL of each diluted particle suspension were placed on formvar-coated copper grids, allowed to settle and dried overnight. Particles were photographed at 14000× and 31,000× magnification in a Philips EM 410 transmission electron microscope (Philips Electron Optics, Eindhoven, The Netherlands) using a magnification standard.

For scanning electron microscopy (SEM), a drop of each particle suspension was placed on a glass slide precoated with 3 nm platinum/carbon, allowed to settle, drained and air-dried overnight before it was coated with platinum/carbon at an angle of 650 under continuous rotation of the sample. The particles were photographed at 6,000× to 60,000× magnification in a Hitachi S-5000 field emission scanning electron microscope (Hitachi Instruments Inc., San Jose, Calif.) using a magnification standard. Particle sizes were determined by measuring the diameters of 125 randomly selected particles of each type on TEM photographs.

Determination of nanoparticle surface area and porosity:

The specific surface area of the aluminum oxide nanoparticles was determined by nitrogen adsorption using the multipoint BET method (Brunauer et al., *J. Am. Chem. Soc.* 60: 309–319 (1938)] on a Quantachrome Autosorb 1 Automated Gas Sorption System, and by mercury porosimetry on a Quantachrome Autoscan 60 mercury porosimeter. Pore size, pore volume and pore surface area were determined by mercury porosimetry (mercury intrusion analysis) [Washburn, E. W., *Proc. Natl. Acad. Sci. USA* 7: 115–116 (1921)]. Both analyses were performed by Quantachrome Corp. (Boynton Beach, Fla.).

Experimental Design

Figure 2:
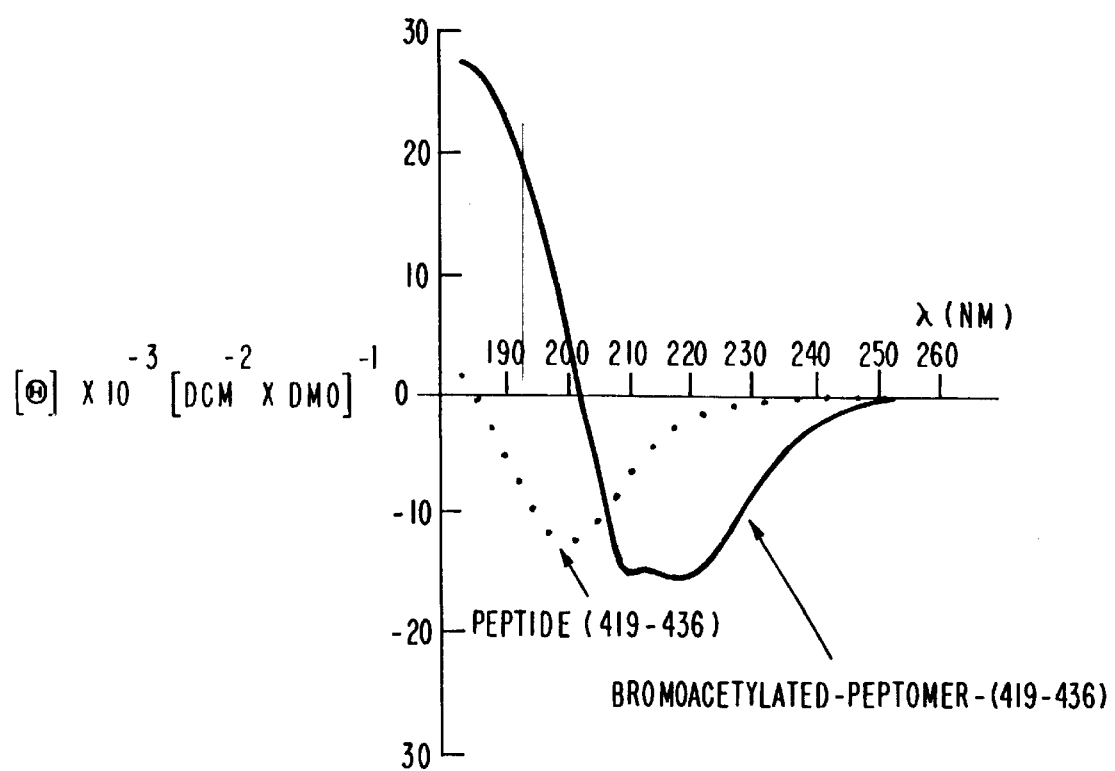
FIG. 2 is a graph showing a conformational study of N-$\epsilon$-bromoacetylated $HIV_{MN}$gp120 C4 peptide constructs.

Experiment 1: Synthesis Of The $HIV_{MN}$ gp120 C4 Domain Peptomer-Aluminum Oxide Conjugates As previously stated, peptomers are polymers composed of head-to-tail linked synthetic peptides. The peptomer of choice for this HIV spatially aligned conjugated composition is a homopolymer of 18-mer oligopeptides comprised by the amino sequence: KIKQIINMWQEVGKAMYAC. As reported in the scientific literature, the first 17 amino acids of this sequence motif represent amino acids 419–436 of gp160, the HIV-$1_{MN}$ gp120 precursor protein. The sequence is reported to be a highly conserved linear epitope in the fourth constant region (C4) of gp120 (between hypervariable regions V4 and V5). It is also said to be an essential part of the CD4 receptor binding site of gp120 and it was shown to previously give rise to virus-neutralizing antibodies.

The $HIV_{MN}$ gp120 domain peptomer aluminum oxide nanoparticles were prepared by separately synthesizing the peptomer antigen and the metallic oxide particles; and conjugating both compounds in a terminal step as is outlined in Reaction Schemes I and II. Reaction Scheme I summarizes the synthesis of the $HIV_{MN}$ gp120 C4 domain peptomer. The C4 peptide used here has the amino acid sequence, KIKQIINMWQEVGKAMYAC-amide. Reaction Scheme II summarizes the synthesis of the $HIV_{MN}$ gp120 C4 domain peptomer nanoparticles.

Initially, the peptide monomer for the preparation of the peptomer was synthesized as C-terminal amide on an automated peptide synthesizer. To allow subsequent head-to-tail polymerization via the intended thioether linkages, an additional cysteine, not present in HIV-$1_{MN}$ gp120 at this position, was placed at the carboxy terminal end of the peptide chain. At the amino terminus, a bromoacetyl moiety was introduced by reacting the N-terminal amine of the immobilized, side-chain-protected peptide with bromoacetic acid anhydride (Reaction Scheme I). The entire bifunctional peptide was then deprotected and released from the resin by anhydrous hydrogen fluoride—conditions which had been shown previously not to affect the integrity of the N-α-bromoacetyl moiety [Robey and Fields, *Anal. Biochem.* 177: 373–377 (1989)]. To prevent premature polymerization or cyclization after removal of the sulfhydryl protecting group, all subsequent steps involving the monomeric peptide were carried out under acidic conditions. Typical yields of crude N-α-bromoacetyl-derivatized cysteine-containing peptide were between 50 and 70%. After preparative HPLC, 30% of the expected pure peptide was obtained.

Autopolymerization of the N-α-bromoacetyl-derivatized, cysteine-containing peptide was initiated by dissolving the purified peptide in aqueous buffer at slightly alkaline pH (pH 8.0). The reaction was performed at a high monomer concentration (≧10 mg/ml) to minimize cyclization reactions. This reaction is summarized by Reaction Scheme I. Under such conditions, the reaction was almost complete after 3 hours—at which time most of the detectable free thiols had been consumed. However, as longer polymer chains may be formed preferentially towards the end of the reaction, a prolonged reaction time of 21 hours was allowed. As expected, the resulting product was not a homogeneous polymer of distinct molecular weight but rather a mixture of peptide oligomers of different chain length. This is shown by FIG. 1 and the data of Table E1 below. The preparation shown in Lane 1 of FIG. 1 was used for the preparation of the conjugate without further size fractionation or enrichment for a particular oligomer species.

FIG. 1 shows the gel analysis of the $HIV_{MN}$ gp120 C4 domain peptomer as a silver stained molecule in a reducing 10–20% polyacrylamide/SDS gel. Lane 1 shows a peptomer of the large scale preparation used for conjugate preparation. Lane 2 shows the molecular weight standards for the analysis.

Notably, initial attempts to utilize the N-α-bromoacetyl groups that were remaining after termination of the autopolymerization reaction for conjugating the peptomer onto the thiol-modified aluminum oxide nanoparticles were not successful. To generate reproducible conditions, the peptomer was therefore end-capped by completely removing the reactive groups at the head and tail of the polymer chain before it was prepared for "side on" conjugation by N-ε-bromoacetylation of the lysine side chains. This is summarized by Reaction Scheme II. Bromoacetylation of the lysines was carried out with a 3-fold molar excess of ε-amino groups to N-succinimidyl bromoacetate in order to guarantee that the labeling occurred statistically in only one out of the three lysines present in a peptide unit. N-ε-bromoacetylation of the lysines with the activated ester proceeded smoothly, consuming ~84% of the derivatizable amine (28% of the total ε-amino groups) within 15 mins. The randomly bromoacetylated peptomer was then used without further purification for reaction with the thiol-modified particles. Bromoacetylation of the peptomer did not effect the amount of α-helix in the peptomer as compared with the non-bromoacetylated educt. The CD spectrum is illustrated by FIG. 2. As shown, FIG. 2 is a conformational study of N-ε-bromoacetylated C4 peptide constructs. CD spectra of N-Ac-peptide-(419–436) (- - - -) and N-ε-bromoacetylated peptomer-(419–436)(———). The bromoacetylated peptomer looked virtually identical to the nonbromoacetylated form reported earlier in the scientific literature. For comparison, the monomeric peptide CD spectrum is given as the broken line shown in FIG. 2, and this data shows that the peptide itself has very little, if any, helical conformation in phosphate buffer, pH 7.2.

The thiol-modified, metallic oxide particles were prepared from plain α-aluminum oxide nanoparticles as depicted in Reaction Scheme II. First, the surface of the corundum powder was cleaned and activated for subsequent derivatization by treatment with hot dilute nitric acid. To introduce a primary amino function onto the surface of the cleaned aluminum oxide nanoparticles they were reacted with (3-aminopropyl)-triethoxysilane (Reaction Scheme II). Assuming that a surface load of 2 μMol/m$^{2-}$ is characteristic for a silane monolayer on a ceramic surface and the specific surface area of the aluminum oxide nanoparticles is 12 m$^2$/g (as stated in Table E2), the silanizing reagent was applied in a 175-fold molar excess. The high particle dispersity (2.5% (v/v) alumina in solvent), in combination with the vast excess of silanizing reagent, effectively prevented crosslinking of the particles as evidenced by the less than 10% increase of the mean particle diameters from before to after the silanization. This is revealed by the data of Table E2 below.

After the surface-attached (3-aminopropyl)-triethoxysilane was sintered onto the particles, the amount of covalently coupled 3-aminopropyl moieties was determined to be 15.9 μMol/g particles which is equivalent to 1.3 μMol amine/m$^2$. The modification proved to be largely resistant to mechanical stress because no significant amine loss could be detected after a 10 min sonication of a particle suspension in a bath sonicator.

To allow conjugation of the N-ε-bromoacetylated peptomer onto the particles via thioether linkages, the amine-modified alumina was reacted at pH 10 with a 100-fold molar excess of N-acetylhomosteinethiolactone (Reaction Scheme II). The formation of free thiol groups was assayed every 15 min with Ellman's reagent. After 45 min of reaction the quantity of free thiol no longer increased and the reaction was terminated. However, though the kinetics of the derivatization could be monitored, it was impossible to determine the absolute amount of free thiol formed because part of the 2-nitro-5-thiobenzoic acid that was released through reaction with the free thiols was nonspecifically adsorbed to the particles.

The thiol-derivatized aluminum oxide nanoparticles then were reacted with the N-ε-lysyl-bromoacetylated peptomer until no more free sulfhydryl groups were detectable in the reaction mixture. Due to the high particle dispersity of 1% (v/v) solids in the reaction mixture no crosslinking of the particles was observed. Instead, the mean particle diameters decreased by 10–20% when compared to the surface-activated and amine-modified alumina. This decrease in particle size is attributed to the abrasion or splitting of the alumina because of mechanical stress during the synthesis. Amino acid analysis of the final conjugate revealed a 55% coupling yield for the peptomer leading to a specific antigen load of 16 mg peptomer per g of aluminum oxide nanoparticles.

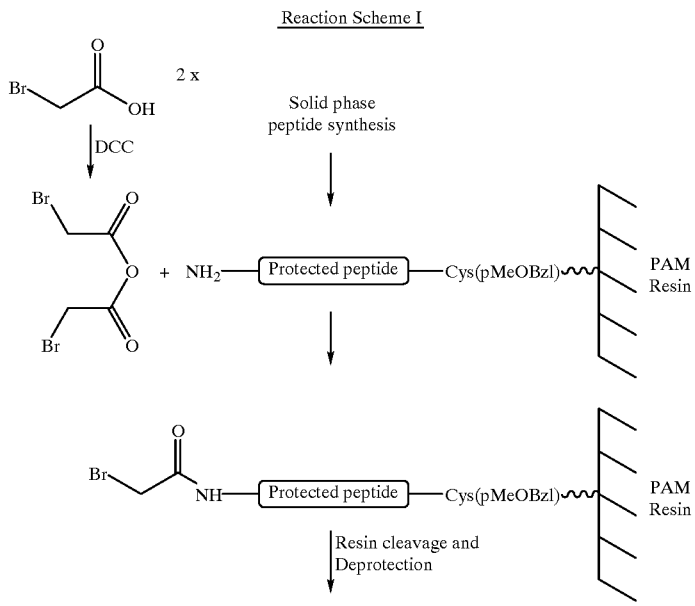

Reaction Scheme I

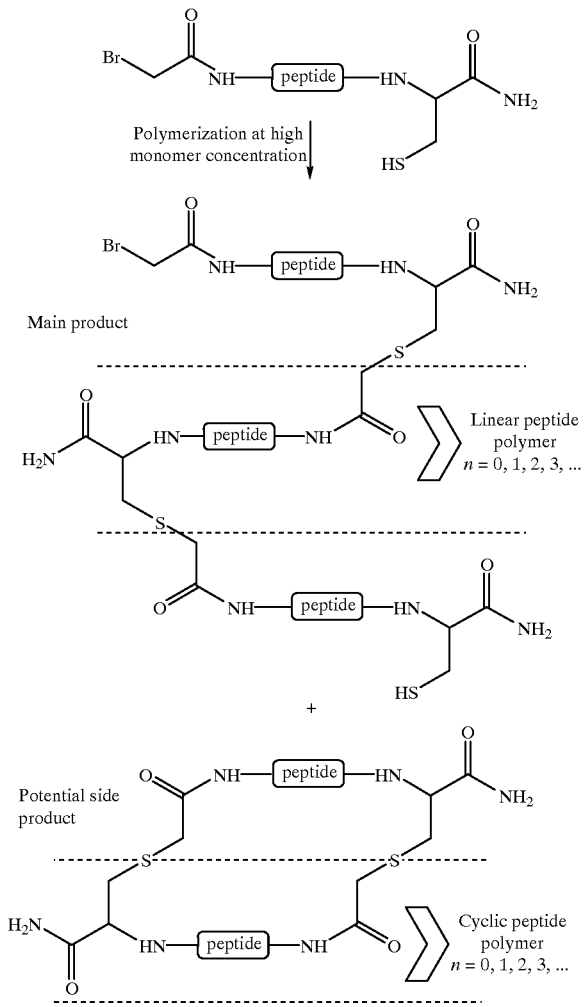
Reaction Scheme II
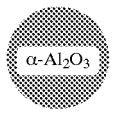
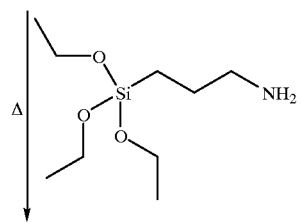
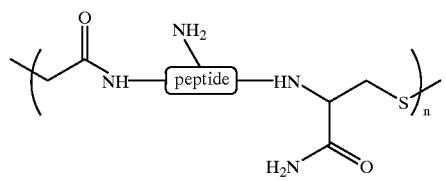

-continued
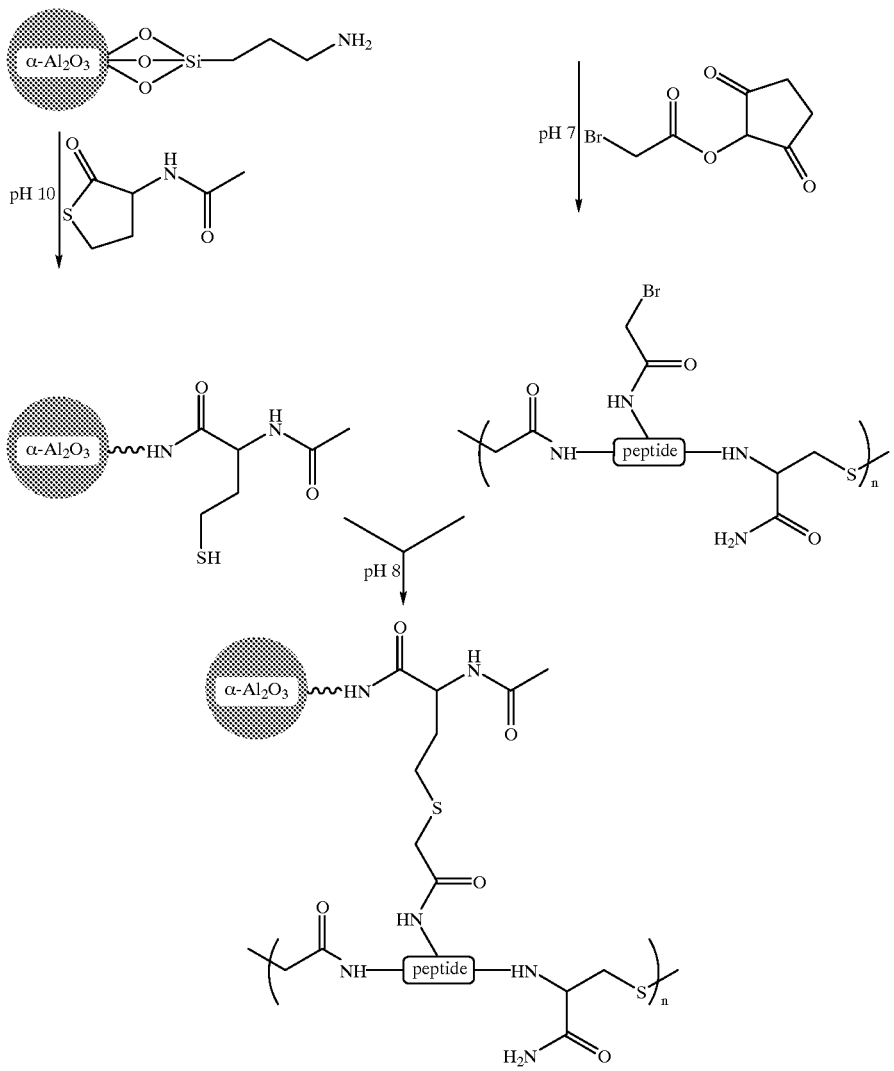

TABLE E1

Degree of Polymerization of $^{HIV}$MN gp120 C4 Domain Peptomer

| Chain length | % of product formed[a] |
|---|---|
| Monomer | 1.7 |
| Dimer | 22.3 |
| Trimer | 12.9 |
| Tetramer | 10.8 |
| Pentamer | 8.0 |
| Hexamer | 6.2 |
| Heptamer | 5.7 |
| Octamer | 4.7 |
| Nonamer | 3.5 |
| Decamer | 2.7 |
| Undecamer | 2.2 |
| Dodecamer | 1.6 |
| >Dodecamer | 17.7 |

[a]Data are derived from a 600 × 600 dpi scan of a silver-stained SDS-PAA gradient gel. Results are given as means of two measurements. Individual measurements differed less than 5% from the given means

TABLE E2

Properties of Aluminum Oxide Nanoparticle Conjugates

| Particle type | Diameter[a] Maximum diameter Mean ± SD (nm) | Maximum diameter Range (nm) | Minimum diameter Mean ± SD (nm) | Minimum diameter Range (nm) | Surface area[b] by MP ($m^2/g$) | Surface area[b] by BET ($m^2/g$) | Conjugate load[c] (μmol/g) |
|---|---|---|---|---|---|---|---|
| Surface-activated | 394 ± 140 | 143–871 | 131 ± 52 | 39–358 | 11.9 | 11.9 | n/a |
| Amino-derivatized | 430 ± 154 | 163–813 | 125 ± 50 | 47–325 | nd | nd | 15.9 |
| Peptomer-derivatized | 355 ± 108 | 158–675 | 113 ± 43 | 42–269 | nd | nd | 7.0 |

[a]Particle diameters were determined by transmission electron microscopy. As most particles were of non-spherical shape, the minimum and maximum diameters and the size ranges are given.
[b]Particle surface area was determined after drying the sample at 300° C. either by mercury porosimetry (MP) or by nitrogen adsorption/desorption (multi-point BET method). Due to the high drying temperature for sample preparation the procedure could not be used for amino- and peptomer-derivatized particles.
[c]Conjugate loads were determined by ninhydrin assay (amino-derivatized particles) or Picotag amino acid analysis (peptomer-derivatized particles). For the peptomer-derivatized particles the molar amounts of peptide units on the particles are given.
n/a, not applicable;
n/d, not determined.

Figure 3:
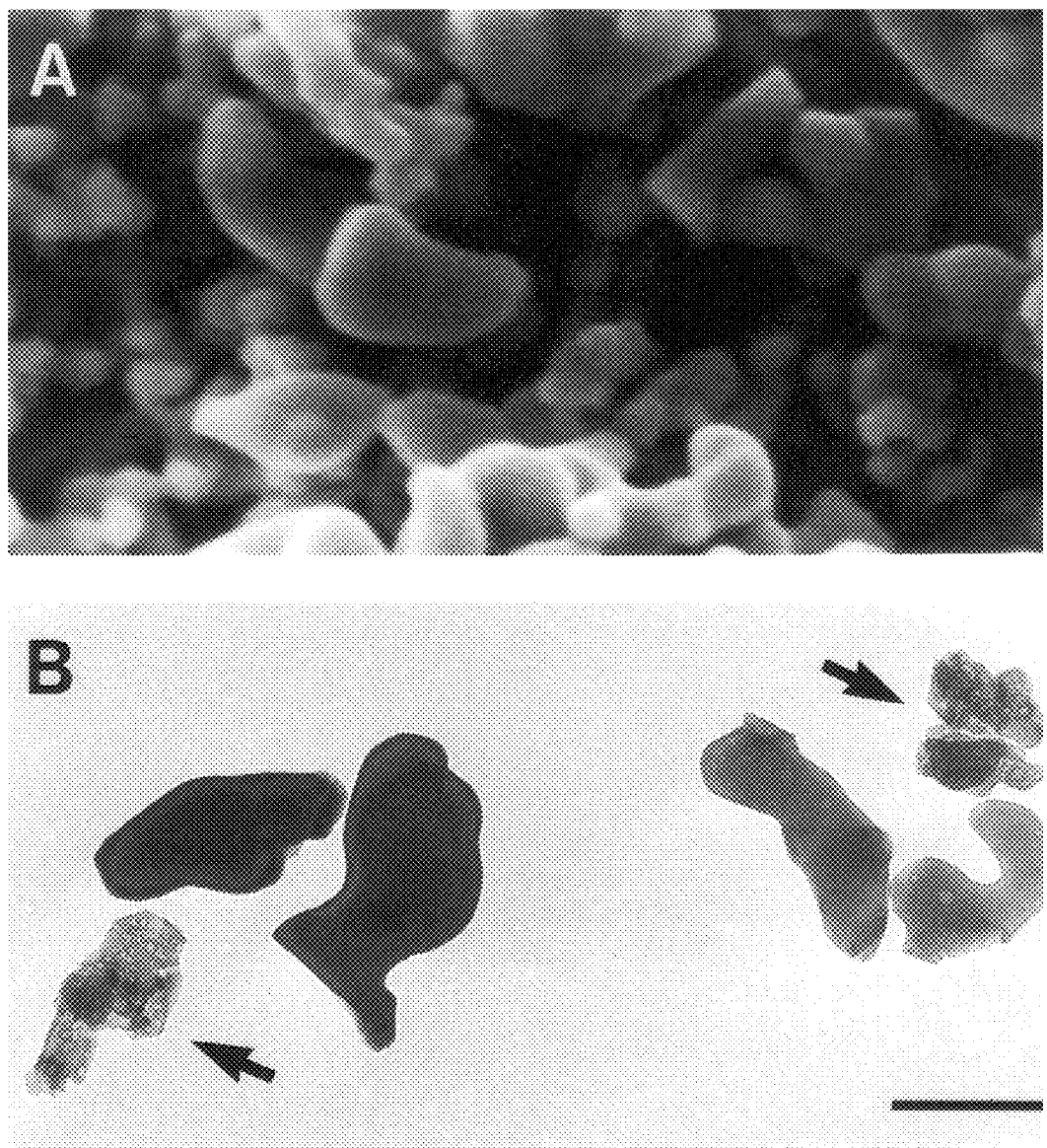
FIGS. 3A and 3B are photographs showing representative scanning and transmission electron microscopic analyses of $HIV_{MN}$ gp120 C4 domain peptomer-derivatized aluminum oxide nanoparticles.
Figure 4:
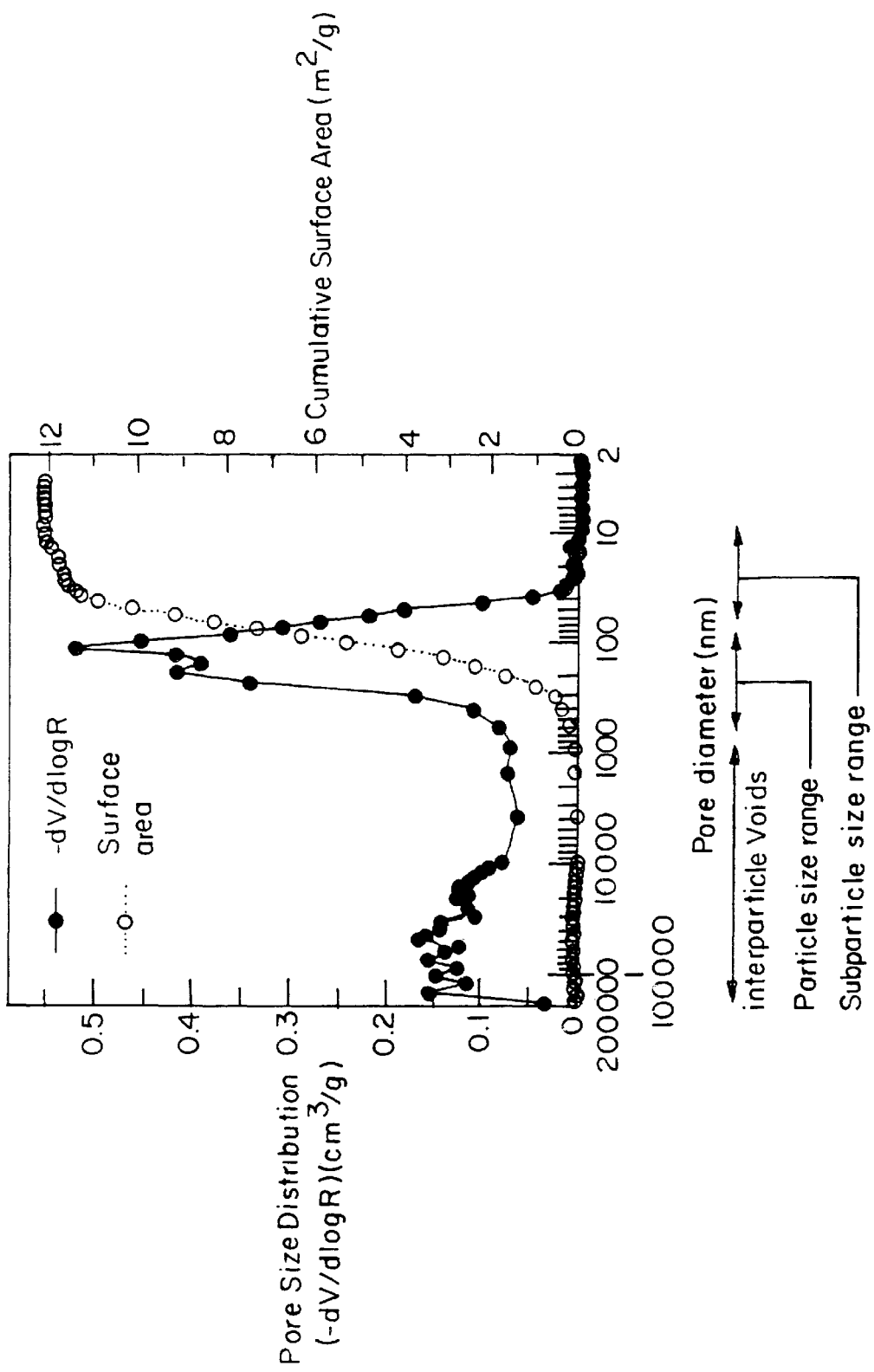
FIG. 4 is a graph showing a pore size analysis of surface activated aluminum oxide nanoparticles as determined by mercury intrusion.

Experiment 2: Characterization Of The $HIV_{MN}$ gp120 C4 Domain Peptomer-Aluminum Oxide Conjugates For use of the peptomer alumina spatially aligned conjugates as systemic or mucosal vaccines, the most important characteristics are deemed to be particle size; porosity, antigen load; the chain length of the attached peptomer; and the stability of the covalent coupling to the carrier. Each of these will be described.

The particle shape and the size of the surface-activated, amine-modified and peptomer-conjugated alumina particles were analyzed by electron microscopy. This is illustrated by FIG. 3. FIG. 3 shows $HIV_{MN}$ gp120 C4 domain peptomer-derivatized aluminum oxide nanoparticles as representative electron micrographs which depict the peptomer-derivatized aluminum oxide nanoparticles. FIG. 3A is a scanning electron micrograph at high particle density which reveals the smooth surface texture displayed by most of the nanoparticles. FIG. 3B is a transmission electron micrograph at low particle density which demonstrates the predominantly elongated shape of the particles and the existence of a "crystalline" subpopulation (arrows) with rugged edges. The scale bar represents 250 nm.

The data show that there were no evident differences in shape or size between the surface-activated starting material and the final peptomer conjugated particle. However, within each sample, two distinct aluminum oxide particle populations were observed in fact. Most of the particles were of ellipsoid or cylindrical shape and displayed a smooth surface texture without sharp corners and edges as seen in FIG. 3A. Nevertheless, a minor fraction of particles consisted of generally smaller sized, rugged particles, which were mostly of non-spherical, irregular shape as illustrated by FIG. 3B. Also, because of the elongated shape of all the particles, the particle size is reported as minimum and maximum diameters (see Table E2). The prepared peptomer-aluminum oxide conjugates exhibited a mean maximum diameter of 355 nm and a mean minimum diameter of 113 nm; this is consistent with the preferred diameter of 300 nm.

The porosity and surface area of the nanometer-sized particles were determined by mercury intrusion and nitrogen adsorption, respectively. Both techniques require the sample to be completely dry. To meet that requirement, samples have to be heated to 300° C. under high vacuum, conditions under which a peptomer or γ-aminopropyl coating is likely to decompose. As the size, shape and surface texture of all samples appeared identical when analyzed by EM, the underivatized, surface-activated alumina is considered to be representative for all particle types in terms of porosity and surface area.

The porosity of the surface-activated alumina was determined by mercury intrusion analysis employing the Washburn relationship and is illustrated by FIG. 4. The differential pore size distribution and the cumulative surface area were obtained. The analysis was carried out with intrusion pressures ranging from 0 to 42,000 $N/cm^2$. The data were calculated assuming a mercury contact angle of 140° and a surface tension of 480 $erg/cm^2$. For greater clarity, only every 20th measured point is shown.

When applying this analytical technique, the interparticle voids (as well as every concave surface curvature of the particles, no matter whether it is a shallow indentation, a deep cavity or a channel) are regarded as pores. In the mercury intrusion analysis of the surface-activated alumina, 40% of the mercury occupied the interparticle voids (≧900 nm) which were not included in the pore size analysis. The remainder intruded into pores between 12 and 900 nm without revealing any distinct pore classes. Instead, a non-parametric pore size distribution was observed with the most frequent pore diameter being 115 nm. 78% of the mercury intruded into pores of 76–575 nm and 13% into pores of 12–66 nm diameter. As the 76–575 nm range corresponds to the mean sizes of the particles themselves, these "pores" must be indentations or bulges on the surface of the alumina rather than true holes or channels, and therefore, must represent the outer surface of the particles. They provide 7.2 $m^2/g$ or 60% of the total specific surface area. The pores of 12–66 nm diameter can be considered true pores or holes representing the inner surface of the particles. Such pores provide 4.7 $m^2/g$ or 40% of the total specific surface area of the particles. This pore diameter also corresponded well with the size of the center holes of some donut-shaped particles that were occasionally observed by EM.

The antigen load of individual conjugated particles was not directly measurable. However, the mean particle diameters, the specific surface area and the specific peptomer load were determined experimentally, and with the aid of these data, the antigen load could be estimated. The estimation is based on the assumption that the mean particle is of cylindrical shape with hemispherical ends, a model that is the best possible approximation for the heterogeneous population of elongated particles which was observed by EM (FIG. 3). For a population of such particles the specific surface area (SSA) is given by Equation 1.

$$SSA = \frac{4 d_{max}}{\rho d_{min}(d_{max} - 1/3\ d_{min})} \qquad [\text{Eq. 1}]$$

where $\rho$ is the density of the alumina as provided by the manufacturer (3.95 g/cm$^3$) and $d_{max}$ and $d_{min}$ are the mean maximum and minimum particle diameters, respectively (see Table E2). Using Equation 1, the specific surface area of the surface activated alumina was calculated to be 8.7±3.5 m$^2$Ig. This mathematical result is in good agreement with the outer surface area of the particles (7.2 m$^2$/g) a s determined by mercury intrusion an alysis; and the total surface area as determined by nitrogen adsorption o r mercury intrusion (as given by Table E2) also less within the margins of error. A cylindrical form with hemispheres on each end is therefore deemed to be an adequate model for the mean particle shape.

Assuming such a particle shape, the number of peptide epitopes per mean particle ($n_e$) is given by Equation 2, $$n_e = \frac{1}{4}\rho\pi d_{min}2(d_{max} - \frac{1}{3}d_{min})\text{SCL N}_A \qquad [\text{Eq. 2}]$$

where $\rho$ is the density of the alumina; $d_{max}$ and $d_{min}$ the mean maximum and minimum diameter; SCL the specific conjugate load; and $N_A$ the Avogadro constant (6.023×10$^{23}$ mol$^{-1}$). Using Equation 2, the $n_e$ was calculated to be 53,000±42,000.

Neither the chain length nor the conformation of the peptomer could be obtained experimentally after it was conjugated via a thioether bond to the particle surface. These properties can therefore only be estimated on the basis of the chain length distribution in the peptomer solutions and the conformation of the N-ϵ-bromoacetylated peptomer prior to conjugation. Assuming that no steric constraints or differences in reactivity between peptomer molecules of different chain length exist, the chain length distribution of the immobilized peptomer would be identical to that of the soluble peptomer preparation. The soluble parent peptomer contained polymerization products ranging from the monomeric starting material to dodecamers and higher—with a median chain length of 5 peptide units; the monomer made up only 1.7% of that preparation (Table E1). Even if a preference for smaller molecules prevailed in the conjugation reaction, the coupling yield of 55% supports the view that at least ~97% of the conjugates consist of dimers and larger molecules.

Experimental Series II

Materials and Methods

Animals:

Female BALB/c (H-2d) and CD-1 (outbred) mice were obtained from Charles River Laboratories (Wilmington, Mass.). They were housed in the Children's Hospital animal facility on standard rodent diet and allowed to acclimate for at least one week before immunization. All animals were 8 weeks of age at the beginning of the immunization experiments.

Antigen preparation and characterization:

All antigens used in the immunization experiments were based on a synthetic peptide representing a linear portion of the C4 domain of HIV-1 gp 120 (corresponding to amino acids 419–436 of the HIV-$1_{MN}$gp120 precursor protein). The general methods for preparation and characterization of the monomeric parent peptides, the polymeric peptomers, and the peptomer particles have been described in detail previously herein (see experimental series I).

Systemic and mucosal immunizations:

The total amounts of $HIV_{MN}$ gp120 C4 domain N-acetylated peptide and peptomer required for each immunization study were dissolved in water and stored in single-use aliquots at −80° C. The peptomer-aluminum oxide conjugated nanoparticles were aliquoted and stored desiccated at room temperature in the dark. Immediately before use the antigen aliquots were warmed to 37° C. and diluted as required with prewarmed buffer. Adjuvants were then added if indicated and the complete formulations were mixed by gentle rocking. Particulate antigen formulations were dispersed by 3–6×5 sec sonication in a water bath sonicator. N-acetylmuramyl-L-alanyl-D-isoglutamine (Muramyldipeptide, MDP; Calbiochem, La Jolla, Calif.) and azide-free cholera toxin (CT; List Biological Laboratories, Campbell, Calif.) were utilized as systemic and mucosal adjuvants, respectively.

Mice were immunized in groups of 4–6 animals. For systemic immunizations, the antigen formulations were injected intraperitoneally (i.p.) in 4 doses given at 2 wk intervals. For mucosal immunizations, the antigen formulations were administered intragastrically (i.g.) in 4 doses at 3 wk intervals under light methoxyflurane anesthesia (Metofane; Pitmann-Moore, Mundelein, Ill.). Antigens were administered intragastrically using 20 gauge×1.5 inch animal feeding needles (Popper & Sons, New Hyde Park, N.Y.), and the animals were deprived of food for 1 h before and 2 h after intubation. Details of the immunization protocols are summarized in Tables E3 and E4.

Sample collection:

Samples were collected according to the schedule shown in Table E4. Blood samples of all immunized animals were drawn before each immunization, and 8–10 days after the last dose, by retroorbial bleed under Avertin anesthesia (300–500 μl Avertin per mouse, i.p.). Avertin was prepared by dissolving tribromoethanol (Chemical Dynamics, South Plainfield, N.J.) 2:1 (w:w) in tert. amyl alcohol; and further diluting this stock solution 1:80 in prewarmed (37° C.) Dulbecco's PBS (D-PBS) [137 mM NaCl, 2.7 mM KCl, 8.1 mM $Na_2HPO_4$, 1.47 mM $KH_2PO_4$; (pH 7.2)] immediately before use. Blood was allowed to clot overnight at room temperature; and sera were separated by centrifugation at 10,000×g for 30 min at 4° C., aliquoted, snap-frozen in liquid $N_2$, and then stored at −80° C. Fecal samples of mucosally-immunized animals were obtained by collecting 6–12 freshly voided fecal pellets per animal. The fecal pellets were kept on ice throughout the entire sampling procedure before they were snap-frozen in liquid $N_2$ and stored at −80° C.

At the end of each study, the animals were killed under Avertin anesthesia by cervical dislocation and the spleens were removed aseptically. Mucosal secretions were collected from mucosally immunized animals using the filter wick method of Haneberg et al., [*Infect. Immun.* 62: 15–23 (1994)]. Briefly, the entire small intestine of the killed and splenectomized animals was removed; placed on an ice-cold glass plate; and the lumen was rinsed in cold D-PBS containing a mixture of protease inhibitors (at a concentration of 1 μg/ml [154 nM] aprotinin (Boehringer Mannheim, Indianapolis, Ind.); 5 μg/ml [10 μM] leupeptin hemisulfate (Calbiochem); 48 μg/ml [200 μM] AEBSF (4-(2-aminoethyl)-benzenesulfonylfluoride (Calbiochem); and 2 μg/ml [6 μM] bestatin hydrochloride (Sigma, St. Louis, Mo.). Preweighed UniWick™ filters (2 cm length, 2.5 mm diameter; Polyfiltronics, Rockland, Mass.) were inserted into the intestine using a glass applicator and allowed to absorb the local secretions for 5–10 min. The secretion-soaked wicks were removed, snap-frozen in liquid $N_2$ and stored at −80° C.

The extraction of immunoglobulins from feces and filter wicks was performed as described by Haneberg et al., [op.

cit.]. Briefly, fecal pellets were lyophilized, homogenized in 20 μl of cold extraction buffer (D-PBS containing 5% (w/v) nonfat dry milk and the protease inhibitor mixture) per mg dry feces; and the solids were removed by 10 min centrifugation at 16,000×g at 4° C. The wicks were extracted with 10 μl extraction buffer per mg secretion. The final fecal and filter extracts were aliquoted, snap-frozen in liquid $N_2$, and then stored at −80° C. The schedule for blood, feces and secretion sampling and for the isolation of splenocytes is summarized by Table E4.

ELISA Assay:

For detection of antibodies against $HIV_{MN}$ gp120 C4 domain peptomer, unrelated peptomer or cholera toxin (CT), a series of microtiter plates (Nunc MaxiSorp; Nalge Nunc International, Rochester, N.Y.) were coated with 100 μl/well of antigen: either 5 μg/ml of the respective peptomer in 10% (v/v) acetic acid, or 2 μg/ml CT in D-PBS. For detection of antibodies against recombinant $HIV_{MN}$ gp120, microtiter plates (Immulon 2; Dynex Technologies, Chantilly, Va.) were coated with 100 μl/well of 5 μg/ml $HIV_{MN}$ rgp120 (Agmed. Bedford, Mass.) in D-PBS. All coating reactions were done overnight at 4° C. in a humidified chamber.

The plates were then washed 3× with 350 μl/well PBST (D-PBS containing 0.05% (v/v) Tween-20) at room temperature using an automated microplate washer (MultiWash; Tri-Continent Scientific Inc., Grass Valley, Calif.); and non-specific binding sites were blocked with 250 μl/well PBS-Blotto (D-PBS containing 5% (w/v) nonfat dry milk) for 30 min at 37° C. and followed by 90 min at room temperature. After another 4 washes with PBST, 100 μl/well serially diluted sera, fecal or filter extracts in PBS-Blotto were applied and the plates were incubated overnight at 4° C.

The plates were washed 4× with PBST, 100 μl/well of horseradish peroxidase-labeled secondary antibody solution were applied and the plates were incubated for 90 min at room temperature. Horseradish peroxidase-labeled secondary reagents were: goat anti-mouse IgG (γ-chain specific; Sigma), 1:2000; goat anti-mouse IgA (α-heavy chain specific; Southern Biotechnology), 1:4000; both diluted with PBS-Blotto. The plates were again washed 6× with PBST and color was developed at room temperature in the dark by adding 100 μl/well 0.4 mg/ml [3.7 mM] o-phenylenediamine (4 mg OPD tablets; Sigma), 0.03% (w/v) [9.8 mM] $H_2O_2$ in phosphate-citrate buffer, pH 5.0 (50.6 mM $Na_2HPO_4$, 24.3 mM citric acid). The reaction was terminated after 30 min by addition of 50 μl/well 2.5 N sulfuric acid and the plates were read at 492 nm on a SPECTRAmax 250 microplate spectrophotoraeter (Molecular Devices Co., Sunnyvale, Calif.).

Preparation of mononuclear cells:

Spleens were removed under aseptic conditions, pooled groupwise, and tissues were ground in RPMI-1640 cell culture medium (GibcoBRL Life Technologies, Gaithersburg, Md.). Single cell suspensions were obtained by teasing out the tissues with 28-gauge needles and cells were harvested by sedimentation at 200×g for 10 min at room temperature. Viable mononuclear cells (MNC) were isolated by centrifuging the resuspended cells (~1×10⁸ cells in 2 ml) on a 3 ml cushion of density gradient separation medium (Lympholite M; Cedarlane Laboratories through Accurate Chemical & Scientific, Westbury, N.Y.) in a 15 ml disposable centrifuge tube at 800×g at room temperature for 15 min. Floating viable MNC were removed; washed three times in RPMI-1640 by resuspending and centrifugation; and were finally suspended to a content of 2×10⁶ cells/ml in RPMI-1640 cell culture medium supplemented with 2 mM glutamine (GibcoBRL), 50 μg/ml amphotericin (Sigma), 0.5 μM 2-mercaptoethanol (Sigma) and 10% heat inactivated fetal calf serum (GibcoBRL).

Lymphocyte stimulation assay:

Lymphocyte stimulation assays were performed in 96-well round bottom plates (Falcon Becton Dickinson, Lincoln Park, N.J.). 150,000 cells/well were cultured in triplicate without or with antigen (2 μM peptide) for five days, pulsed with 0.5 μCi/well of [³H]-thymidine (Amersham, Arlington Heights, Ill.) and harvested 20 hours later. Incorporated [³H]-thymidine was measured by liquid scintillation counting.

Data analysis and statistics:

Antibody responses were expressed as endpoint titers, being the reciprocal of the highest dilution that gave a reading above cut-off. The cut-off was defined to be the upper limit of a 99.75% confidence interval above mean control level and was calculated by t-statistics. In systemic immunizations titers below 50 were considered zero when calculating the means. Titers were transformed logarithmically to obtain geometric means (log (titer+1)) and standard errors of the means (SEM).

For comparisons between two group means unpaired t-tests were used. Multiple (between group) comparisons were performed by one-way analysis of variance (ANOVA) using Fisher's protected least-significant difference at a 5% level of significance. Interactive effects were assessed by 2-factor ANOVA. Results of all statistical analyses were considered significant only if p <0.05. All calculations and statistical analyses were carried out on an Apple PowerPC 7100/66 computer (Apple, Cupertino, Calif.) using the Statview SE+Graphics™ iiprogram (Abacus Concepts, Berkeley, Calif.).

Experimental Design

The peptide-based HIV candidate vaccines that were investigated in this Experiment Series II are derived from a highly conserved linear domain in the fourth constant region (C4) of $HIV_{MN}$ gp120 (between hypervariable regions V4 and V5), which comprises the amino acid sequence: KIK-QIINMWQEVGKAMYA. The sequence motif represents amino acids 419–436 of the HIV-$1_{MN}$ gp160 precursor protein or amino acids 390–407 of the mature gp120 envelope protein. On the basis of this peptide building block, three types of C4 domain antigens differing in polymericity, conformation and physical state were synthesized: (i) a monomeric, soluble form of the peptide, in the following called "peptide"; (ii) a polymeric, soluble derivative of the parent peptide termed "peptomer"; and (iii) a particulate conjugate of aluminum oxide nanoparticles and peptomer designated "peptomer-particles".

The peptide antigen consisted of a homogeneous population of N-acetylated peptide molecules which predominantly display β-sheet (41%) and random-coil conformation (56%) but almost no α-helical structure (2%). In comparison, the peptomer antigen consisted of a heterogeneous population of head-to-tail polymerized peptide molecules with a median chain length of 4 peptide units and a monomer content of 4.2%. Upon polymerization the relative amount of α-helical conformation typically rises to ≧50% while the β-sheet and random coil content decrease to ~30% and <20%, respectively.

The peptomer-particles consisted of an α-aluminum oxide core onto which peptomer molecules were coupled covalently, as described in Experimental Series I. Particles of 350±108×113±43 nm in diameter were loaded with a peptomer preparation of 5 peptide units median chain length to yield a preparation containing 53,000±42,000 peptide units per particle. The relative α-helical content of the peptomer which was coupled via the thioether linkage to the particles had not been affected by the side chain derivatization necessary for the conjugate coupling procedure.

Experiment 3: Systemic Immunization With HIV gp120 C4 Domain Antigens

As the C4 domain of HIV-1 gp120 is known to contain a haplotype restricted murine helper T cell antigenic site, the immunogenicity of C4 domain antigens may vary depending on the mouse strain used for immunization. For that reason the immunogenicity of the peptomer-particle conjugate was tested in outbred CD-1 mice and juxtaposed to that in Balb/c mice (H-$2^d$). After repeated i.p. immunizations with 50 μg peptomer-particle antigen +50 μg MDP adjuvant, a similar time course of anti-C4 domain peptomer IgG responses was observed in both mouse strains. The result is given by Table E5. However, after priming and 3 booster immunizations the humoral immune response was about 20-fold higher in Balb/c than in outbred CD-1 mice and the standard error of the mean was considerably smaller in the inbred mouse strain. For that reason Balb/c mice were used in all subsequent immunization studies.

The three types of synthetic antigen used in this study differed considerably in conformation, polymericity and physical state. In order to identify the individual drawbacks and benefits of each antigen formulation, a comprehensive systemic immunization study with peptide, peptomer and peptomer-particles in the presence and absence of adjuvant was carried out. The dosage and immunization schedules are summarized by Tables E3 and E4.

Figure 5A:
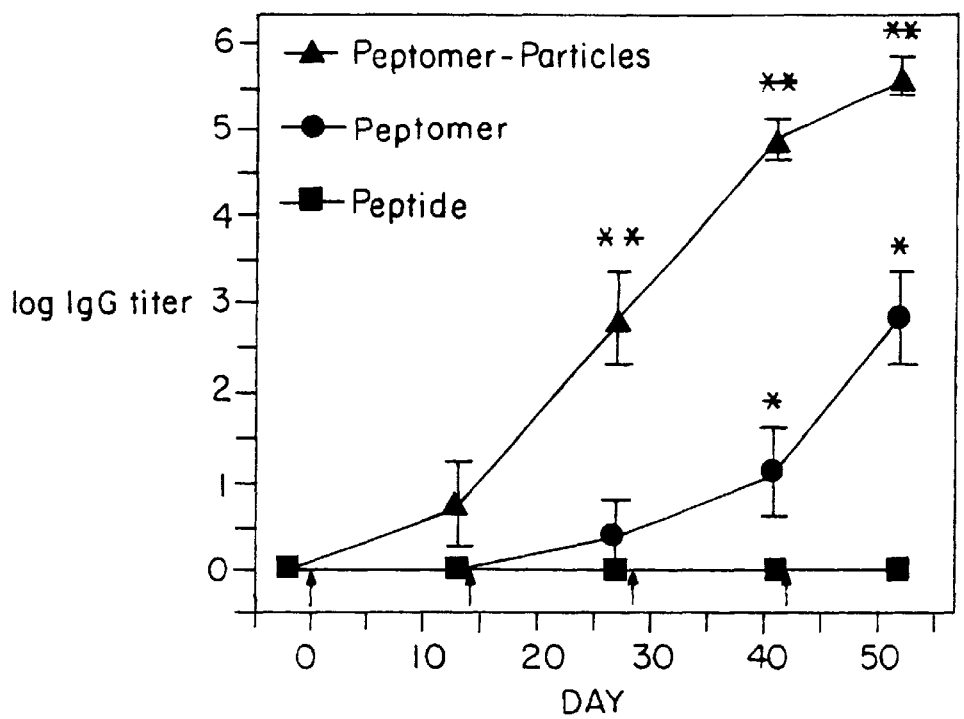
FIGS. 5A and 5B are graphs showing the time course of serum IgG responses against $HIV_{MN}$ gp120 C4 domain peptomer after i.p. immunization with different C4 domain antigens either adjuvant-free or in the presence of muramyl-dipeptide adjuvant as determined by ELISA assay.
Figure 5B:
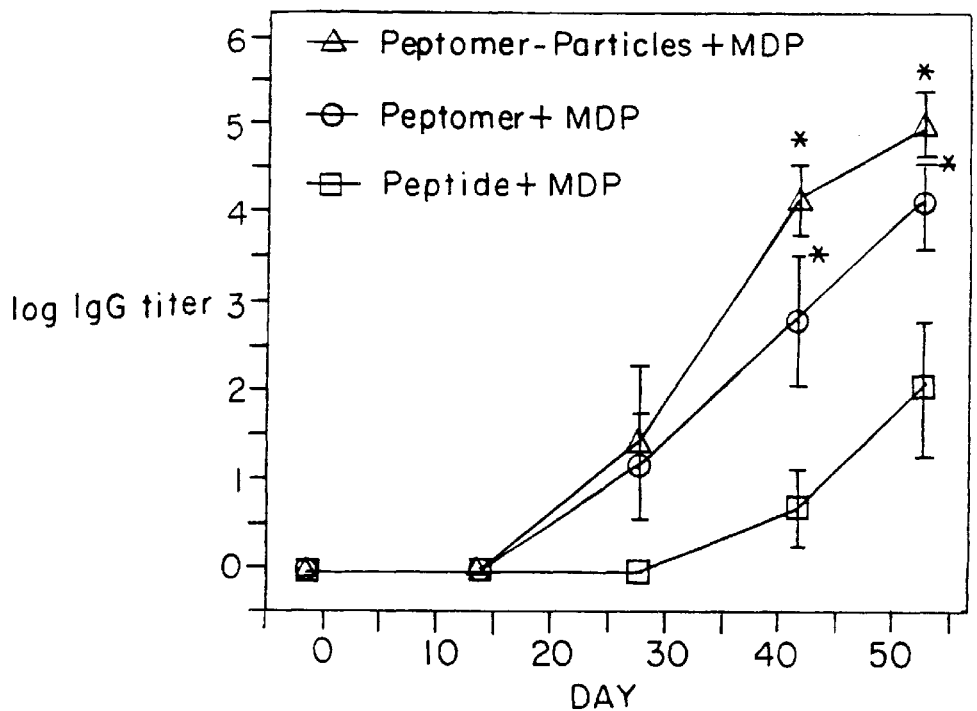

In the absence of MDP, both peptomer and peptomer-particles (but not peptide) gave rise to anti-C4 domain peptomer IgG responses in serum (FIG. 5A). The earliest onset of IgG humoral immune response and the highest level of antibody occurred after immunization with peptomer particles. The MDP adjuvant showed a negative interaction with antigen polymericity that became significant after the third booster immunization (2-factor ANOVA; p <0.03). In the presence of MDP, the response to peptomer-particles was about 4-fold lower than that seen without MDP, while MDP enhanced immune responses to peptomer and raised responses to peptide to detectable levels (FIG. 5B).

Figure 6:
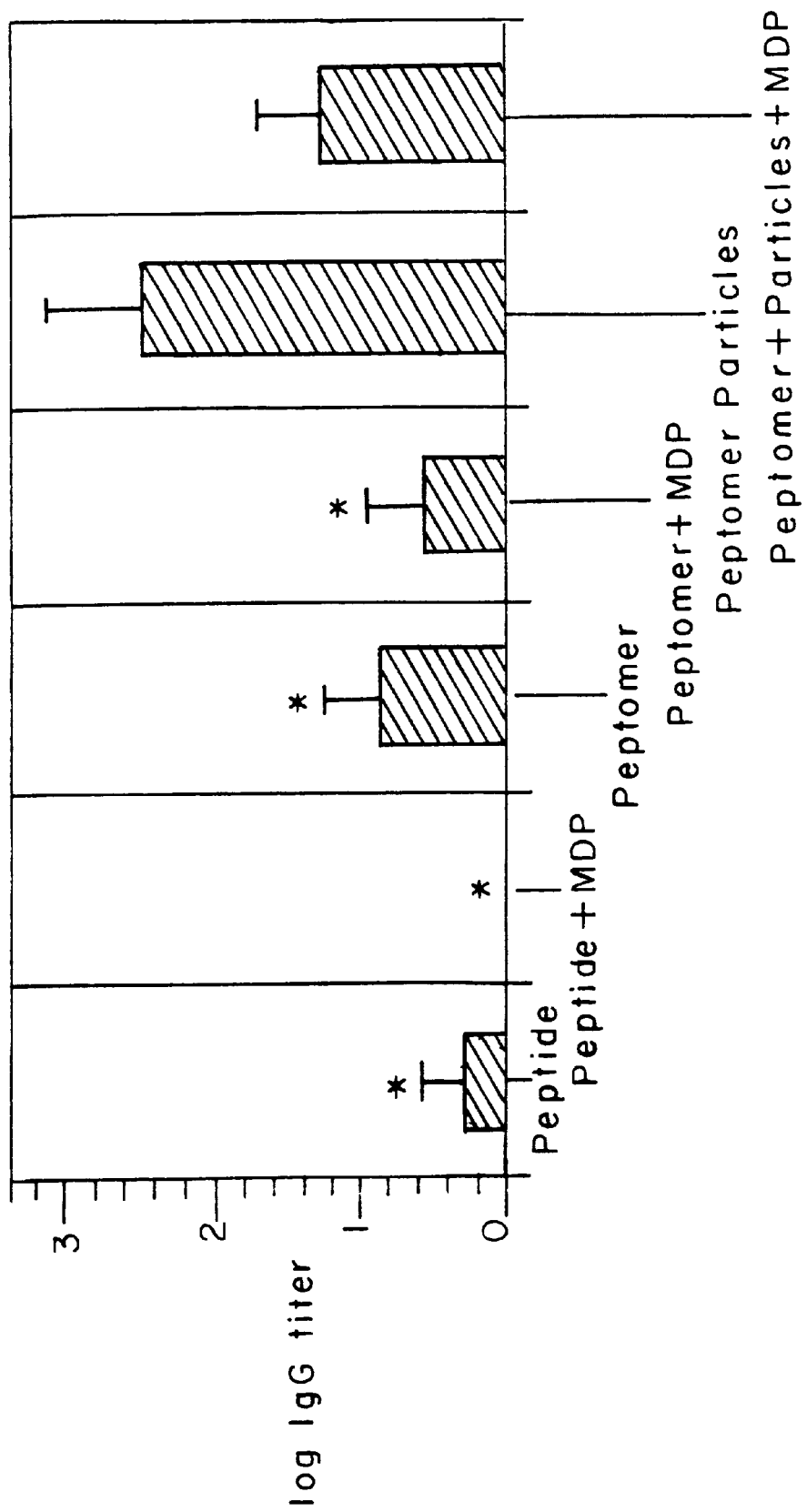
FIG. 6 is a graph showing recognition of recombinant $HIV_{MN}$ gp120 by serum IgG antibodies after i.p. immunization with $HIV_{MN}$ gp120 C4 domain peptomer nanoparticle conjugates.

Superior immunogenicity of the peptomer-particle antigen (the conjugate composition) was also observed when analyzing the crossreactivity of the final anti-C4 domain IgG responses to native gp120. Five out of six animals immunized with peptomer-particles and 3 out of 4 animals immunized with peptomer-particles+MDP recognized baculovirus-expressed HIV$_{MN}$ gp120 in the final bleed. This result is shown by FIG. 6. The mean IgG reactivity against native gp120 in both groups was significantly higher than that generated by the other antigen formulations but no significant differences between the two particle groups were detected in a one-factorial ANOVA.

FIG. 6 shows the recognition of recombinant HIV$_{MN}$ gp120 by antibodies induced after systemic immunization with C4 domain peptomer nanoparticles. Serum IgG induced by i.p. priming and three booster immunizations with different C4 domain antigens were analyzed by ELISA for their reactivity towards baculovirus-expressed HIV$_{MN}$ gp120. The results are expressed as geometric means ±SEM of endpoint titers of 4–6 animals. The asterisk represents immune responses significantly lower than that induced by peptomer-particles [one-factor ANOVA, Fisher's protected least significant difference test, p <0.005.]

Figure 7:
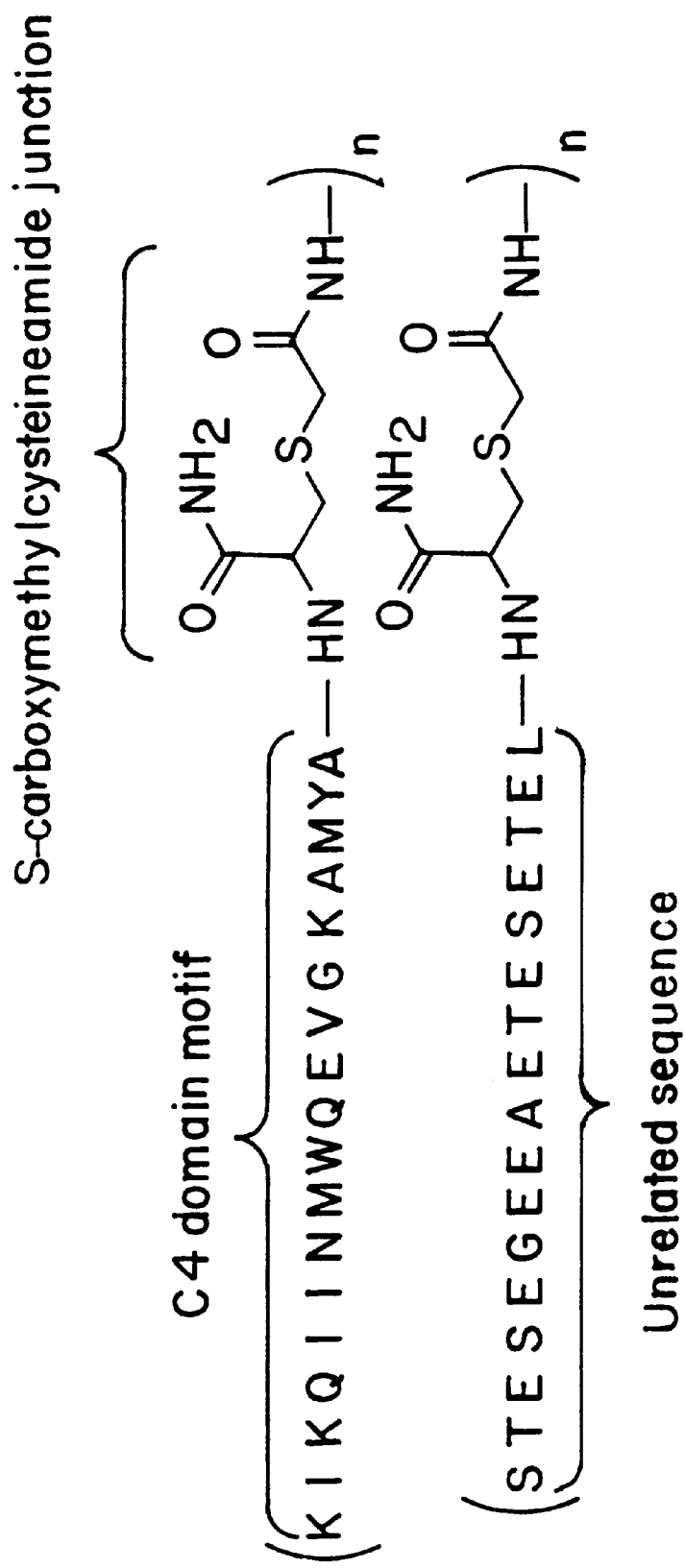
FIG. 7 is a drawing showing the formula structure of the S-carboxymethylcysteineamide peptide-peptide junction of the $HIV_{MN}$gp120 C4 domain peptomer and of a peptomer of unrelated sequence.

In order to rule out an hapten-like effect of the S-carboxymethylcysteineamide junction in the peptomer molecules, the final immune sera of mice immunized with either peptomer or peptomer-particle antigen formulations were tested for their crossreactivity to an unrelated peptomer. The unrelated peptomer molecule contained the same junction between peptides as the C4 domain peptomer antigens but the amino acid sequence of the peptide building blocks was different. This is shown by FIG. 7. FIG. 7 illustrates the structure of the peptide-peptide junction in peptomer molecules. Building blocks of the HIV$_{MN}$ gp120 C4 domain peptomer (upper formula) and of a peptomer of unrelated sequence (lower formula) were used. Both peptomers share a common S-carboxymethylcysteineamide junction but display different amino acid sequences. On the basis of this crossreactivity analysis, no humoral immune response against the S-carboxymethylcysteine junctions in the peptomers could be detected.

Figure 8:
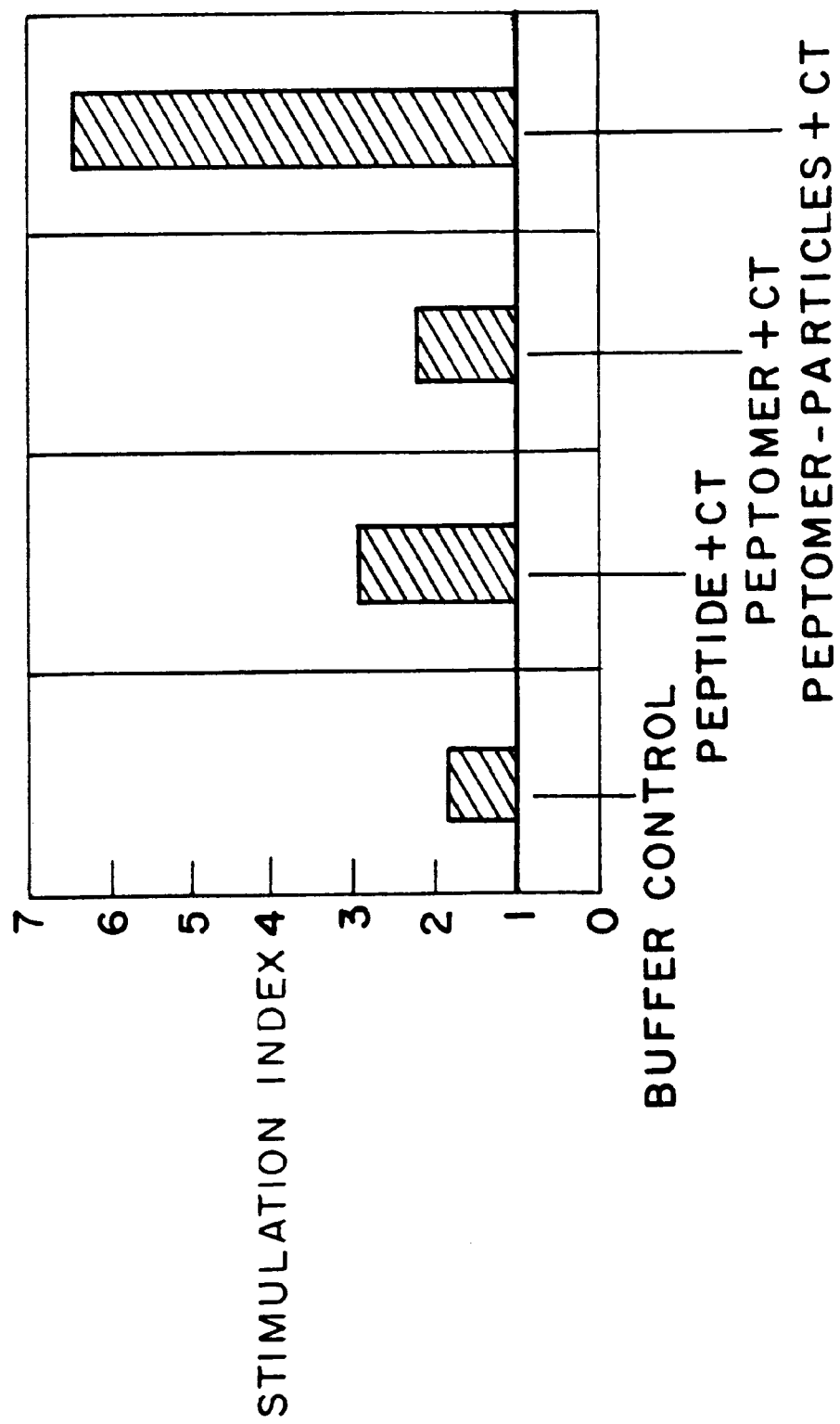
FIG. 8 is a graph showing T-cell activation responses in animals after intragastrical immunization with $HIV_{MN}$ gp120 C4 domain antigens.

As the parent peptide of all HIV-1$_{MN}$ gp120 C4 domain antigens contained a helper T cell epitope, the question— whether the gp120 C4 domain antigen formulations were able to recruit T cell help after systemic immunization—was investigated. Systemic priming with peptide alone did not induce a proliferative response in spleen MNC upon in vitro rechallenge with antigen. This is revealed by FIG. 8. FIG. 8 shows the T cell activation after systemic immunization with HIV$_{MN}$ C4 domain antigens. The animals were immunized by i.p. priming and three booster immunizations with different C4 domain antigen formulations. Splenocytes were prepared 11 days after the last booster immunization; pooled groupwise; and the proliferative responses assayed in triplicate each by [$^3$H] thymidine incorporation upon in vitro restimulation with 2 μM peptide antigen. The results are expressed as stimulation indices, i.e., the ratio of thymidine incorporation in the presence and absence of peptide antigen stimulus.

Experiment 4: Mucosal Immunization With HIV gp120 C4 Domain Antigens.

Peptide, peptomer and peptomer-particle antigen were also tested for their mucosal immunogenicity. To allow a direct comparison, the same batches of antigen as in the systemic immunization studies were used—though antigen dose, adjuvant and immunization regimen were adjusted accordingly. For the intragastrical immunizations, a four times higher antigen dose was used and cholera toxin was added as adjuvant throughout. Sodium bicarbonate buffer was used instead of PBS in order to neutralize the stomach acid and the immunization regimen was extended to three week instead of two week intervals (see Tables E3 and E4).

After priming and three booster immunizations, sera, feces and small intestinal secretions were analyzed for the presence of cholera toxin (CT) and gp 120 C4 domain peptomer-specific immunoglobulins. While a strong cholera toxin-specific antibody response was found in all samples tested, no antibodies against gp120 C4 domain peptomer could be detected in sera, feces and small intestinal secretions.

Although B cell responses were lacking completely after intragastrical immunization with HIV$_{MN}$ gp120 C4 domain antigens, stimulation of T cells was detected after priming and three booster immunizations. This is shown by FIG. 8.

Note that FIG. 8 shows the T cell activation response after mucosal immunization with HIV$_{MN}$ C4 domain antigens. Animals were immunized by i.g. priming and three booster immunizations with different C4 domain antigen formulations. Splenocytes were prepared 8 days after the last booster immunization; pooled groupwise; and the proliferative responses assayed in triplicate each by [$^3$H] thymidine incorporation upon in vitro restimulation with 2 μM peptide antigen. The results are expressed as stimulation indices, i.e. ratio of thymidine incorporation in the presence and absence of peptide antigen stimulus. The proliferative response after rechallenge with peptide antigen was most prominent with splenocytes of mice immunized with peptomer-particles+ CT, exhibiting a stimulation index of 6.4.

The present invention is not to be limited in scope nor restricted in form except by the claims appended hereto.

TABLE E3

Experimental Setup of the Immunization Studies

| Immunization group | Route of immunization | No. of animals | Antigen formulation |
|---|---|---|---|
| | Systemic | | Total application volume: 500 μl of |
| Buffer control | (i.p.) | 6 | D-PBS |
| Peptide | (i.p.) | 6 | 50 μg Peptide in buffer |
| Peptide + MDP | (i.p.) | 6 | 50 μg Peptide + 50 μg MDP in buffer |
| Peptomer | (i.p.) | 6 | 50 μg Peptomer in buffer |
| Peptomer + MDP | (i.p.) | 6 | 50 μg Peptomer + 50 μg MDP in buffer |
| Peptomer − Particles | (i.p.) | 6 | 50 μg Peptomer on $Al_2O_3$-particles in buffer |
| Peptomer − Particles + MDP | (i.p.) | 4 | 50 μg Peptomer on $Al_2O_3$-particles + 50 μg MDP in buffer |
| | Mucosal | | Total application volume: 300 μl of |
| Buffer control | (i.g.) | 6 | 100 mM Sodium bicarbonate |
| Peptide + CT | (i.g.) | 6 | 200 μg Peptide + 5 μg CT in buffer |
| Peptomer + CT | (i.g.) | 6 | 200 μg Peptomer + 5 μg CT in buffer |
| Peptomer − Particles + CT | (i.g.) | 5 | 200 μg Peptomer on $Al_2O_3$-particles + 5 μg CT in buffer |

TABLE E4

Schedule of the Immunizations and Sampling Experiments

| Route of Immunization | No. and time of immunizations | Time of sample collections | | | |
|---|---|---|---|---|---|
| | | Blood | Feces | Intestinal secretions | Spleen cells |
| Systemic | 4 doses on days 0, 14, 28, 42 | on days −2, 13, 27, 41, 52 | — | — | on day 53 |
| Mucosal | 4 doses on days 0, 21, 42, 63 | on days −1, 20, 41, 62, 71 | on days −2, 19, 40, 61, 70 | on day 71 | on day 71 |

TABLE E5

Anti $^{HIV}$MN gp120 C4 Domain
Peptomer Serum IgG Responses in
Different Mouse Strain[a]

| | log IgG titer[b] | |
|---|---|---|
| Day | CD1 (outbred) | Balb/c (H-$2^d$) |
| −1 | <2 | <2 |
| 13 | <2 | <2 |
| 27 | 3.37 ± 0.22 | 3.6 ± 0.11 |
| 42 | 3.95 ± 0.25 | 4.83* ± 0.11 |
| 52 | 4.48 ± 0.34 | 5.76* ± 0.14 |

[a]Mice were immunized systemically with peptomer − particles + MDP and bled as outlined in Tables E3 and E4.
[b]Titers were determined by ELISA against C4 domain peptomer and are expressed as geometric means ± SEM of endpoint titers of 6 animals.
*Asterisks indicate significant differences in the anti-C4 domain peptomer serum IgG responses of CD1 and Balb/c mice (unpaired, two-tailed t-test, $p < 0.01$)

What is claimed is:

1. A spatially aligned conjugated composition suitable as an immunogen to be administered to a living subject for inducing an immune response against a prechosen infectious agent, said conjugated composition comprising:

at least one chemically modified substance wherein said chemical modification provides said substance with at least one reactive entity and a fixed spatial orientation for forming a thioether bond and wherein said substance is selected from the group consisting of haptens and antigens immunologically representative of the prechosen infectious agent;

a plurality of chemically substituted metallic oxide particles wherein said chemical substitution provides said particles with at least one corresponding reactive moiety for forming a thioether bond and wherein said metallic oxide particles have a diameter size ranging from about 10–10,000 nanometers; and at least one thioether bond joining said modified substance in a controlled orientation to said nanometer-sized substituted metallic oxide particles to form a plurality of spatially aligned conjugates.

2. The spatially aligned conjugated composition as recited in claim 1 wherein said chemically modified substance comprises a polysaccharide composition.

3. The spatially aligned conjugated composition as recited in claim 1 wherein said chemically modified substance comprises a proteinaceous composition.

4. The spatially aligned conjugated composition as recited in claim 1 wherein said metallic oxide particles are composed of aluminum oxide.

5. The spatially aligned conjugated composition as recited in claim 1 wherein said metallic oxide particles are composed of at least one selected from the group consisting of aluminum oxide ($Al_2O_3$), titanium dioxide ($TiO_2$), zirconium dioxide ($ZrO_2$), hydroxyapatite ($Ca_5(OH)(PO_4)_3$), silicon dioxide ($SiO_2$), magnesium oxide (MgO), yttrium oxide ($Y_2O_3$), scandium oxide ($Sc_2O_3$), and lanthanum oxide ($La_2O_3$).

6. A fluid immunogen to be administered to a living subject for inducing an immune response against a prechosen infectious agent, said fluid immunogen comprising:

a biocompatible carrier fluid; and a predetermined quantity of a spatially aligned conjugated composition suspended in said carrier fluid, said spatially aligned conjugated composition being comprised of (i) at least one chemically modified substance wherein said chemical modification provides said substance with at least one reactive entity and a fixed spatial orientation for subsequently forming a thioether bond and wherein said substance is selected from the group consisting of haptens and antigens immunologically representative of the prechosen infectious agent, (ii) a plurality of chemically substituted metallic oxide particles wherein said chemical substitution provides said particles with at least one corresponding reactive moiety for forming a thioether bond and wherein said metallic oxide particles have a diameter size ranging from about 10–10,000 nanometers, and (iii) at least one thioether bond joining said modified substance in a controlled orientation to said nanometer-sized substituted metallic oxide particles to form a plurality of spatially aligned conjugates.

7. The fluid immunogen as recited in claim 6 wherein said biocompatible fluid carrier is selected from the group consisting of physiological saline, a aqueous solution containing electrolytes, and a buffered aqueous liquid.

8. The fluid immunogen as recited in claim 6 wherein said biocompatible fluid carrier is an oil-based formulation selected from the group consisting of petroleum, mineral oil and water-in-oil emulsions.

9. The fluid immunogen as recited in claim 6 wherein the prechosen infectious agent is a virus.

10. The fluid immunogen as recited in claim 6 wherein the prechosen infectious agent is a bacterium.

11. The fluid immunogen as recited in claim 6 wherein the prechosen infectious agent is one selected from the group consisting of rickettsiae, chlamydiae, mycoplasms, protozoa, fungal and parasitic infectious agents.

* * * * *